(12) United States Patent
Urnov et al.

(10) Patent No.: US 9,752,140 B2
(45) Date of Patent: *Sep. 5, 2017

(54) METHODS AND COMPOSTIONS FOR TARGETED GENOMIC DELETION

(71) Applicant: Sangamo BioSciences, Inc., Richmond, CA (US)

(72) Inventors: Fyodor Urnov, Richmond, CA (US); Jianbin Wang, Richmond, CA (US); Michael C. Holmes, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/007,569

(22) Filed: Jan. 27, 2016

(65) Prior Publication Data
US 2016/0177290 A1 Jun. 23, 2016

Related U.S. Application Data

(63) Continuation of application No. 14/502,773, filed on Sep. 30, 2014, now Pat. No. 9,249,428, which is a continuation of application No. 13/310,263, filed on Dec. 2, 2011, now abandoned, said application No. 14/502,773 is a continuation-in-part of application No. 13/784,634, filed on Mar. 4, 2013, which is a continuation of application No. 11/304,981, filed on Dec. 15, 2005, now Pat. No. 8,409,861, which is a continuation-in-part of application No. 10/912,932, filed on Aug. 6, 2004, now Pat. No. 7,888,121.

(60) Provisional application No. 61/458,957, filed on Dec. 3, 2010, provisional application No. 60/649,515, filed on Feb. 3, 2005, provisional application No. 60/493,931, filed on Aug. 8, 2003, provisional application No. 60/518,253, filed on Nov. 7, 2003, provisional application No. 60/530,541, filed on Dec. 18, 2003, provisional application No. 60/542,780, filed on Feb. 5, 2004, provisional application No. 60/556,831, filed on Mar. 26, 2004, provisional application No. 60/575,919, filed on Jun. 1, 2004.

(51) Int. Cl.
| | | |
|---|---|---|
| C12N 15/87 | (2006.01) | |
| C12N 15/82 | (2006.01) | |
| C12N 15/90 | (2006.01) | |
| C12N 15/10 | (2006.01) | |
| C12N 15/85 | (2006.01) | |
| C07H 21/04 | (2006.01) | |

(52) U.S. Cl.
CPC ....... *C12N 15/102* (2013.01); *C12N 15/8213* (2013.01); *C12N 15/907* (2013.01); *C12N 2800/80* (2013.01)

(58) Field of Classification Search
None
See application file for complete search history.

(56) References Cited

U.S. PATENT DOCUMENTS

| | | | |
|---|---|---|---|
| 4,665,184 A | 5/1987 | Dervan et al. | |
| 4,795,184 A | 1/1989 | Dervan et al. | |
| 4,942,227 A | 7/1990 | Dervan et al. | |
| 5,356,802 A | 10/1994 | Chandrasegaran | |
| 5,436,150 A | 7/1995 | Chandrasegaran | |
| 5,487,994 A | 1/1996 | Chandrasegaran | |
| 5,789,155 A | 8/1998 | Dervan et al. | |
| 5,789,538 A | 8/1998 | Rebar et al. | |
| 5,792,640 A | 8/1998 | Chandrasegaran | |
| 5,916,794 A | 6/1999 | Chandrasegaran | |
| 5,925,523 A | 7/1999 | Dove et al. | |
| 5,945,577 A | 8/1999 | Stice et al. | |
| 5,948,678 A | 9/1999 | Dujon et al. | |
| 5,955,341 A | 9/1999 | Kang et al. | |
| 6,007,988 A | 12/1999 | Choo et al. | |
| 6,013,453 A | 1/2000 | Choo et al. | |
| 6,077,710 A | 6/2000 | Susko-Parrish et al. | |
| 6,140,081 A | 10/2000 | Barbas | |
| 6,140,466 A | 10/2000 | Barbas et al. | |
| 6,147,276 A | 11/2000 | Campbell et al. | |
| 6,200,759 B1 | 3/2001 | Dove et al. | |
| 6,242,568 B1 | 6/2001 | Barbas et al. | |
| 6,265,196 B1 | 7/2001 | Chandrasegaran | |
| 6,326,166 B1 | 12/2001 | Pomerantz et al. | |
| 6,331,658 B1 | 12/2001 | Cooper et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,534,261 B1 | 3/2003 | Cox et al. | |
| 6,903,185 B2 | 6/2005 | Kim et al. | |

(Continued)

FOREIGN PATENT DOCUMENTS

| | | |
|---|---|---|
| EP | 0 957 165 | 11/1999 |
| GB | 238237 | 12/1999 |

(Continued)

OTHER PUBLICATIONS

Abremski, et al., "Bacteroiphage P1 Site Specific Recombination," *JBC* 259:1509-1514 (1984).
Aggarwal, et al., "Novel Site-Specific DNA Endonucleases," *Current Opinion in Structural Biology* 8:19-25 (1998).
Akopian, et al., "Chimeric Recombinases With Designed DNA Sequence Recognition," *Proc. Natl. Acad. Sci. USA* 100:8688-8691 (2003).
Bai, et al., "Genetic Co-Inactivation of Macrophonage-and T-Trophic HIV-1 Cehmokine Coreceptors CCR-5 and CXCR-4 by Intrakines," *Gene Therapy* 5:984-994 (1998).
Baubonis, et al., "Genomic Targeting With Purified CRE Recombinase," *Nucleic Acids Res.* 21:2025-2029 (1993).

(Continued)

*Primary Examiner* — Nancy J Leith
(74) *Attorney, Agent, or Firm* — Pasternak Patent Law; Susan Abrahamson

(57) ABSTRACT

Disclosed herein are compositions and methods for generating chromosomal translocations and targeted deletions of specific lengths and at specific locations the genome of cell.

6 Claims, 6 Drawing Sheets

(56) References Cited

U.S. PATENT DOCUMENTS

| | | | |
|---|---|---|---|
| 7,153,949 | B2 | 12/2006 | Kim et al. |
| 7,888,121 | B2 | 2/2011 | Urnov et al. |
| 8,409,861 | B2 | 4/2013 | Guschin et al. |
| 9,249,428 | B2 * | 2/2016 | Urnov .................. C12N 15/102 |
| 2002/0022021 | A1 | 2/2002 | Emerson |
| 2002/0107214 | A1 | 8/2002 | Choulika et al. |
| 2002/0110898 | A1 | 8/2002 | Choulika et al. |
| 2002/0152488 | A1 | 10/2002 | Cooper et al. |
| 2003/0131365 | A1 | 7/2003 | Cooper et al. |
| 2003/0232410 | A1 | 12/2003 | Liljedahl et al. |
| 2004/0019002 | A1 | 1/2004 | Choulika et al. |
| 2004/0121357 | A1 | 6/2004 | Franklin |
| 2005/0026157 | A1 | 2/2005 | Baltimore et al. |
| 2005/0064474 | A1 | 3/2005 | Urnov et al. |
| 2005/0208489 | A1 | 9/2005 | Carroll et al. |
| 2006/0063231 | A1 | 3/2006 | Li et al. |
| 2006/0188987 | A1 | 8/2006 | Guschin et al. |
| 2007/0134796 | A1 | 6/2007 | Holmes et al. |
| 2007/0218528 | A1 | 9/2007 | Miller et al. |
| 2008/0015164 | A1 | 1/2008 | Collingwood |
| 2008/0131962 | A1 | 6/2008 | Miller et al. |
| 2008/0159996 | A1 | 7/2008 | Ando et al. |
| 2009/0068164 | A1 | 3/2009 | Segal et al. |
| 2009/0089890 | A1 | 4/2009 | D'Halluin et al. |
| 2009/0133152 | A1 | 5/2009 | Lyznik et al. |
| 2009/0305346 | A1 | 12/2009 | Miller et al. |
| 2010/0218264 | A1 | 8/2010 | Cui et al. |
| 2011/0145940 | A1 | 6/2011 | Voytas et al. |
| 2011/0201055 | A1 | 8/2011 | Doyon et al. |
| 2011/0201118 | A1 | 8/2011 | Yang et al. |
| 2011/0207221 | A1 | 8/2011 | Cost et al. |
| 2011/0281361 | A1 | 11/2011 | DeKelver et al. |
| 2011/0287512 | A1 | 11/2011 | Paschon et al. |
| 2011/0301073 | A1 | 12/2011 | Gregory et al. |
| 2014/0065667 | A1 | 3/2014 | Guschin et al. |

FOREIGN PATENT DOCUMENTS

| | | |
|---|---|---|
| WO | WO 95/09233 | 4/1995 |
| WO | WO 95/19431 A1 | 7/1995 |
| WO | WO 96/06166 | 2/1996 |
| WO | WO 96/40882 | 12/1996 |
| WO | WO 97/47758 | 12/1997 |
| WO | WO 98/37186 | 8/1998 |
| WO | WO 98/53057 | 11/1998 |
| WO | WO 98/53058 | 11/1998 |
| WO | WO 98/53059 | 11/1998 |
| WO | WO 98/53060 | 11/1998 |
| WO | WO 98/54311 | 12/1998 |
| WO | WO 00/09755 | 2/2000 |
| WO | WO 00/27878 | 5/2000 |
| WO | WO 00/28008 | 5/2000 |
| WO | WO 00/42219 | 7/2000 |
| WO | WO 00/46385 | 8/2000 |
| WO | WO 00/46386 | 8/2000 |
| WO | WO 00/63365 | 10/2000 |
| WO | WO 01/05961 | 1/2001 |
| WO | WO 01/19981 | 3/2001 |
| WO | WO 01/40798 | 6/2001 |
| WO | WO 01/60970 | 8/2001 |
| WO | WO 01/66717 | 9/2001 |
| WO | WO 01/88197 | 11/2001 |
| WO | WO 02/04488 | 1/2002 |
| WO | WO 02/16536 | 2/2002 |
| WO | WO 02/077227 | 10/2002 |
| WO | WO 02/099084 | 12/2002 |
| WO | WO 03/016496 A2 | 2/2003 |
| WO | WO 03/080809 | 10/2003 |
| WO | WO 03/087341 | 10/2003 |
| WO | WO 2004/037977 A2 | 5/2004 |
| WO | WO 2007/014275 | 2/2007 |
| WO | WO 2007/139982 A2 | 12/2007 |
| WO | WO 2009/042163 A2 | 4/2009 |
| WO | WO 2010/079430 A1 | 7/2010 |
| WO | WO 2010/107493 A2 | 9/2010 |
| WO | WO 2010/117464 A1 | 10/2010 |

OTHER PUBLICATIONS

Beerli, et al., "Engineering Polydactyl Zinc-Finger Transcription Factors," *Nature Biotechnology* 20:135-141 (2000).

Bibikova, et al., "Enhancing Gene Targeting With Designed Zinc Finger Nucleases," *Science* 300:764 (2003) Including Supporting Online Materials.

Bibikova, et al., "Stimulation of Homologous Recombination Through Targeted Cleavage by Chimeric Nucleases," *Molecular and Cellular Biology* 21(1):289-297 (2001).

Bibikova, et aL, "Targeted Chromosomal Cleavage and Mutagenisis in *Drosophilia* Using Zinc-Finger Nucleases," *Genetics* 161:1169-1175 (2002).

Bitinaite, et al., "Foki Dimerization Is Required for DNA Cleavage," *Proc. Natl. Acad. Sci*. 95(18):10570-10575 (1998).

Bonas, et al., "Genetic and Structural Characterization of the Avirulence Gene AVRBS3 From Xanthomonas Campestris PV. Vesicatoria," *Mol. Gen. Genet.* 218(1):127-136 (1989).

Brenneman, et al., "Stimulation of Intrachromosomal Homologous Recombination in Human Cells by Electroporation With Site Specific Endonucleases," *Proc. Natl. Acad. Sci. USA* 93:3608-3612 (1996).

Brisson, et al., "Expression of a Bacterial Gene in Plants by Using a Viral Vector," *Nature* 310:511-514 (1984).

Broglie, et al., "Light Regulated Expression of a Pea Ribulose-1, 5-Biphosphate Carboxylase Small Subunit Gene in Transformed Plant Cells," *Science* 224:838-843 (1984).

Brunet, et al., "Chromosomal Translocations Induced at Specified Loci in Human Stem Cells," *Proc. Natl. Acad. Sci.* 106(26):10620-10625 (2009).

Campbell, et al., "Sheep Cloned by Nuclear Transfer From a Cultured Cell Line," *Nature* 380:64-66 (1996).

Cappechi, et al., "Altering the Genome by Homologous Recombination," *Science* 244:1288-1292 (1989).

Chandrasegaran, et al., "Chimeric Restriction Enzymes: What Is Next?," *Biol. Chem*. 380:841-848 (1999).

Chevalier, et al., "Design, Activity, and Structure of a Highly Specific Artificial Endonuclease," *Molecular Cell* 10:895-905 (2002).

Choulika, et al., "Induction of Homologous Recombination in Mammalian Chromosomes by Using the I-SCEI System of *Saccharomyces cerevisiae,*" *Molecular and Cellular Biology* 15(4):1968-1973 (1995).

Cohen-Tannoudji, et al., "I-SCEI-Induced Gene Replacement at a Natural Locus in Embryonic Stem Cells," *Molecular and Cellular Biology* 18(3):1444-1448 (1998).

Corruzzi, et al., "Tissue Specific and Light-Regulated Expression of a Pea Nuclear Gene Encoding the Small Subunit of Ribulose-1, 5-Biphosphate Carboxylase," *Embo. J.* 3:1671-1679 (1984).

Desjarlais, et al., "Towards Rules Relating Zinc Finger Protein Sequences and DNA Binding Site Preferences," *Proc. Natl. Acad. Sci. USA* 89:7345-7349 (1992).

Desjarlais, et al., "Use of a Zinc-Finger Consensus Sequence Framework and Specificity Rules to Design Specific DNA Binding Proteins," *Proc. Natl. Acad. Sci. USA* 90:2256-2260 (1993).

Donoho, et al., "Analysis of Gene Targeting and Intrachromosomal Homologous Recombination Stimulated by Genomic Double-Strand Breaks in Mouse Embryonic Stem Cells," *Molecular and Cellular Biology* 18(7):4070-7078 (1998).

Dreier, et al., "Development of Zinc Finger Domains for Recognition of the 5'-ANN-3' Family of DNA Sequences and Their Use in the Construction of Artificial Transcription Factors," *JBC* 276(31):2466-29478 (2001).

Elliot, et al., "Gene Conversion Tracts From Double Strand Break Repair in Mammalian Cells," *Molecular and Cellular Biology* 18(1):93-101 (1998).

Elrod-Erickson, et al., "Binding Studies With Mutants of ZIF268," *J. Biol. Chem.* 274(27):19281-19285(1999).

(56) References Cited

OTHER PUBLICATIONS

Evans, et al., "Establishment in Culture of Pluripotential Cells From Mouse Embryos," *Nature* 292:154-156 (1981).
Furguson-Smith, "Imprinting and the Epigenetic Asymmetry Between Parental Genomes," *Science* 293:1086-1089 (2001).
Gorlich, et al., "Nucleocytoplasmic Transport," *Science* 271:1513-1518 (1996).
Gowda, et al., "Identification of Promoter Sequences for the Major RNA Transcripts of Figwort Mosaic and Peanut Chloritic Streak Viruss (Caulimovirus Group)," *J. Cell. Biochem.* 13D:301 (1989).
Greisman, et al., "A General Strategy for Selecting High-Affinity Zinc Finger Proteins for Diverse DNA Target Sites," *Science* 275:657-661 (1997).
Gu, et al., "Deletion of a DNA Polymerase B Gene Segment in T Cells Using Cell Type-Specific Gene Targeting," *Science* 265:103-106 (1994).
Gu, et al., "Independent Control of Immunogoblin Switch Recombination at Individual Switch Regions Evidenced Through CRE-IOXP-Mediated Gene Targeting," *Cell* 73:1155-1164 (1993).
Gurley, et al., "Upstream Sequences Required for Efficient Expression of a Soybean Heat Shock Gene," *Mol. Cell. Biol.* 6:559-565 (1986).
Hanson, et al., "Analysis of Biological Selections for High-Efficiency Gene Targeting," *Mol. Cell. Biol.* 15:45-51 (1995).
Heuer, et al., "Repeat Domain Diversity of AVRBS3-Like Genes in Ralstonia Solanacearum Strains and Association With Host Preferences in the Field," *Appl. Environ. Microbiol.* 73(13):4379-4384 (2007).
Hicks, et al., "Three Classes of Nuclear Import Signals Bind to Plant Nuclei," *Plant Physiol.* 107:1055-1058 (1995).
Huang, et al., "SPLASE: A New Class IIS Zinc-Finger Restriction Endonuclease With Specificity for SP1 Binding Sites," *Journal of Protein Chemistry* 15(5):481-489 (1996).
Jaenisch, "Transgenic Animals," *Science* 240:1468-1474 (1988).
Jallepalli, et al., "Securin Is Required for Chromosomal Stability in Human Cells," *Cell* 105:445-457 (2001).
Jasin, "Genetic Manipulation of Genomes With Rare-Cutting Endonucleases," *Trends Genet.* 12:224-228 (1996).
Jasin, et al., "Gene Targeting at the Human CD4 Locus by Epitope Addition," *Genes & Development* 4:157-166 (1990).
Jeggo et al., "Identification of Genes Involved in Repair of DNA Double-Strand Breaks in Mammalian Cells," *Radiation Research* 150:S80-S91 (1998).
Johnson, et al., "Double-Strand-Break-Induced Homologous Recombination in Mammalian Cells," *Biochemical Society Transactions* 29:196-201 (2001).
Kay, et al., "A Bacterial Effector Acts as a Plant Transcription Factor and Induces a Cell Size Regulator," *Science* 318(5850):648-651 (2007).
Khanna, et al., "DNA Double-Strand Breaks: Signaling, Repair and the Cancer Connection," *Nature Genetics* 27:247-254 (2001).
Kim et al., "Construction of a Z-DNA-Specific Restriction Endonuclease," *Proc. Natl. Acad. Sci. USA* 94:12875-12879 (1997).
Kim, et al., "Chimeric Restriction Endonuclease," *Proc. Natl. Acad. Sci. USA* 91:883-887 (1994).
Kim, et al., "Chimeric Restriction Enzyme: GAI4 Fusion to Foki Cleavage Domain," *Biol. Chem.* 379:489-495 (1998).
Kim, et al., "Hybrid Restriction Enzymes: Zinc Finger Fusions to FOK I Cleavage Domain," *Proc. Natl. Acad. Sci.* 93(3):1156-1160 (1996).
Kim, et al., "Insertion and Deletion of Mutants of FOKI Restriction Endonuclease," *Journal of Biol. Chem.* 269(50):31978-31982 (1994).
Klein, et al., "Transformation of Microbes, Plants and Animals by Particle Bombardment," *Bio/Techniques* 10:286-291 (1992).
Klein, et al., "High-Velocity Microprojectiles for Delivering Nucleic Acids Into Living Cells," *Nature* 327:70-73 (1987).
Kuehn, et al., "A Potential Animal Model for Lesch-Nyhan Syndrome Through Introduction of HPRT Mutations Into Mice," *Nature* 326:295-298 (1987).

Lai, et al., "Production of A-1,3-Galctosyltransferase Knockout Pigs by Nuclear Transfer Cloning," *Science* 295:1089-1092 (2002).
Li, et al., "Alteration of the Cleavage Distance of FOKI Restriction Endonuclease by Insertion Mutagenesis," *Proc. Natl. Acad. Sci. USA* 90:2764-2768 (1993).
Li, et al., "Functional Domains in FOKI Restriction Endonuclease," *Proc. Natl. Acad. Sci. USA* 89:4275-4279 (1992).
Liu, et al., "Validated Zinc Finger Protein Designs for All 16 GNN DNA Triplet Targets," *J. Biol. Chem.* 277(6):3850-3856 (2002).
Mattaj, et al., "Nucleocytoplasmic Transport: The Soluble Phase," *Annu. Rev. Biochem.* 67:265-306 (1998).
McCreath, et al., "Production of Gene-Targeted Sheep by Nuclear Transfer From Cultured Somatic Cells," *Nature* 405:1066-1069 (2000).
Nahon, et al., "Targeting a Truncated Ho-Endonuclaese of Yeast to Novel DNA Sites With Foreign Zinc Fingers," *Nucleic Acids Research* 26(51:1233-1239 (1998).
Odell, et al., "Identification of DNA Sequences Required for Activity of the Cauliflower Mosaic Virus 35S Promoter," *Nature* 313:810-812 (1985).
Oliver-Bonet, et al., "Aneuploid and Unbalanced Sperm in Two Translocation Carriers: Evaluation of the Genetic Risk," *Mol. Hum. Reprod.* 8(10):958-963 (2002).
Orlando, et al., "Zinc-Finger Nulease-Driven Targeted Integration Into Mammalian Genomes Using Donors With Limited Chromosomal Homology," *Nucleic Acids Research* 38(15):e152 (2010).
Pabo, et al., "Design and Selection of Novel CYS2HIS2 Zinc Finger Proteins," *Annu. Rev. Biochem.* 70:313-340 (2001).
Perez, et al., "Establishment of HIV-1 Resistance in CD4+ T Cells by Genome Editing Using Zinc-Finger Nucleases," *Nat. Biotechnol.* 26(7):808-816 (2008).
Porteus, et al., "Chimeric Nucleases Stimulate Gene Targeting in Human Cells," *Science* 300:763 (2003).
Porteus, et al., "Efficient Gene Targeting Mediated by Adeno-Associated Virus and DNA Double-Strand Breaks," *Mol. Cell. Biol.* 23:3558-3565 (2003).
Puchta, et al., "Homologous Recombination in Plant Cells is Enhanced by In Vivo Induction of Double Strand Breaks Into DNA by a Site-Specific Endonuclease," *Nucleic Acids Res.* 21:5034-5040 (1993).
Rebar, et al., "Induction of Angiogenesis in a Mouse Model Using Engineered Transcription Factors," *Nat. Med.* 8(12): 1427-1432 (2002).
Rebar, et al., "Zinc Finger Phage: Affinity Selection of Fingers With New DNA-Binding Specificities," *Science* 263:671-673 (1994).
Ridout III, et al., "Nuclear Cloning and Epigenetic Reprogramming of the Genome," *Science* 293:1093-1098 (2001).
Rouet, et al., "Expression of a Site-Specific Endonuclease Stimulates Homologous Recombination in Mammalian Cells," *Proc. Natl. Acad. Sci. USA* 91:6064-6068 (1994).
Rouet, et al., "Introduction of Double-Strand Breaks Into the Genome of Mouse Cells by Expression of a Rare-Cutting Endonuclease," *Molecular and Cellular Biology* 14(12):8096-8106 (1994).
Sanford, et al., "An Improved, Helium-Driven Biolistic Device," *Tech.-A J. of Meth. In Cell and Mol. Biol.* 3:3-16 (1991).
Santiago, et al., "Targeted Gene Knockout in Mammalian Cells by Using Engineered Zinc Finger Nucleases," *Proc. Natl. Acad. Sci.* 105(15):5809-5814 (2008).
Sargent, et al., "Repair of Site-Specific Double-Strand Breaks in a Mammalian Chromosome by Homologous and Illegitimate Recombination," *Molecular and Cellular Biology* 17(1):267-277 (1997).
Schnieke, et al., "Human Factor IX Transgenic Sheep Produced by Transfer of Nuclei From Transfected Fetal Fibroblasts," *Science* 278:2130-2133 (1997).
Schornack, et al., "Gene-For-Gene-Mediated Recognition of Nuclear-Targeted AVRBS3-Like Bacterial Effector Proteins," *J. Plant Physiol.* 163(3): 256-272 (2006).
Sedivy, et al., "Positive Genetic Selection for Gene Disruption in Mammalian Cells by Homologous Recombination," *Proc. Natl. Acad. Sci. USA* 86:227-231 (1989).

(56) References Cited

OTHER PUBLICATIONS

Segal, et al., "Endonuclease-Induced, Targeted Homologous Extrachromosomal Recombination in *Xenopus* Oocytes," *Proc. Natl. Acad. Sci. USA* 92:806-810 (1995).
Segal, et al., "Toward Controlling Gene Expression at Will: Selection and Design of Zinc Finger Domains Recognizing Each of the 5'-GNN-3' DNA Target Sequences," *Proc. Natl. Acad. Sci. USA* 96:2758-2763 (1999).
Segal, D. J., "The Use of Zinc Finger Peptides to Study the Role of the Specific Factor Binding Sites in the Chromatin Environment," *Methods* 26:76-83 (2002).
Sera, et al., "Rational Design of Artificial Zinc-Finger Proteins Using a Nondegenerate Recognition Code Table," *Biochemistry* 41:7074-7081 (2002).
Severin, et al., "Heat-Inducible Hygromycin Resistance in Transgenic Tobacco," *Plant Mol. Biol.* 15:827-833 (1990).
Shi, et al., "Specific DNA-RNA Hybrid Binding by Zinc Finger Proteins," *Science* 268:282-284 (1995).
Shillito, et al., "Protoplast Isolation and Transformation," *Pint. Mol. Bio.-A Prac. App.*, Shaw, ed., IRL Press, 161-186 (1988).
Shin, et al., "A Cat Cloned by Nuclear Transplantation," *Nature* 415:859 (2002).
Smih, et al., "Double Strand Breaks at the Target Locus Stimulate Gene Targeting in Embryonic Stem Cells," *Nuc. Acids Res.* 23(24):5012-5019 (1995).
Smith, et al., "A Detailed Study of the Substrate Specificity of a Chimeric Restriction Enzyme," *Nuc. Acids Res.* 27(2):674-681 (1999).
Smith, et al., "Requirements for Double-Strand Cleavage by Chimeric Restriction Enzymes With Zinc Finger DNA Recognition Domains," *Nuc. Acids Res.* 28(17):3361-3369.
Sternberg, et al., "Bacteriophage P1 Site-Specific Recombination," *J. Mol. Biol.* 150:467-507 (1981).
Taghian, et al., "Chromosomal Double-Strand Breaks Induce Gene Conversion at High Frequency in Mammalian Cells," *Mol. and Cell. Biol.* 17(11):6386-6393 (1997).
Takamatsu, et al., "Expression of Bacterial Chloramphenicol Acetyltransferase Gene in Tobacco Plants Mediated by TMV-RNA," *EMBO J.* 6:307-311 (1987).
Thierry, et al., "Cleavage of Yeast and Bacteriophage T& Genomes at a Single Site Using the Rare Cutter Endonuclease I-SCE I," *Nucleic Acids Res.* 19:189-190 (1991).
Urnov, et al., "Highly Efficient Endogenous Human Gene Correction Using Designed Zinc-Finger Nucleases," *Nature* 435(7042):646-651 (2005).
Velten, et al., "Isolation of a Dual Plant Promoter Fragment From the TI Plasmid of Agrobacterium Tumefaciens," *EMBO J.* 3:2723-2730 (1984).
Wall, et al., "Structure of the Multimodular Endonuclease FOKI Bound to DNA," *Nature* 388:97-100 (1997).
Wilmut, et al., "Viable Offspring Derived From Fetal and Adult Mammalian Cells," *Nature* 385:810-813 (1997).
Wilson, J. H., "Pointing Fingers at the Limiting Step in Gene Targeting," *Nature Biotechnology* 21(7):759-760 (2003).
Wolfe, et al., "Beyond the Recognition Code: Structures of Two CYS2HIS2 Zinc Finger/Tata Box Complexes," *Structure* 9:717-723 (2001).
Wolfe, et al., "DNA Recognition by CYS2HIS2ZINC Finger Proteins," *Annu. Rev. Biophys. Biomol. Struct.* 3:183-212 (1999).
Xu, et al., "Engineering a Nicking Endonuclease N. ALWL by Domain Swapping," *PNAS USA* 98(23):12990-12995 (2001).
Yanez, et al., "Therapeutic Gene Targeting," *Gene Therapy* 5:149-159 (1998).
Zhou, et al., "Impaired Macrophage Function and Enhanced T Cell-Dependent Immune Response in Mice Lacking CCR5, The Mouse Homologue of the Major HIV-1 Coreceptor," *The Journal of Immunology* 160:4018-4025 (1998).
Zuffrey, et al., "Woodchuck Hepatitis Virus Posttranscriptional Regulatory Element Enhances Expression of Transgenes Delivered by Retroviral Vectors," *Journal of Virology* 73(4):2886-2892 (1999).

\* cited by examiner

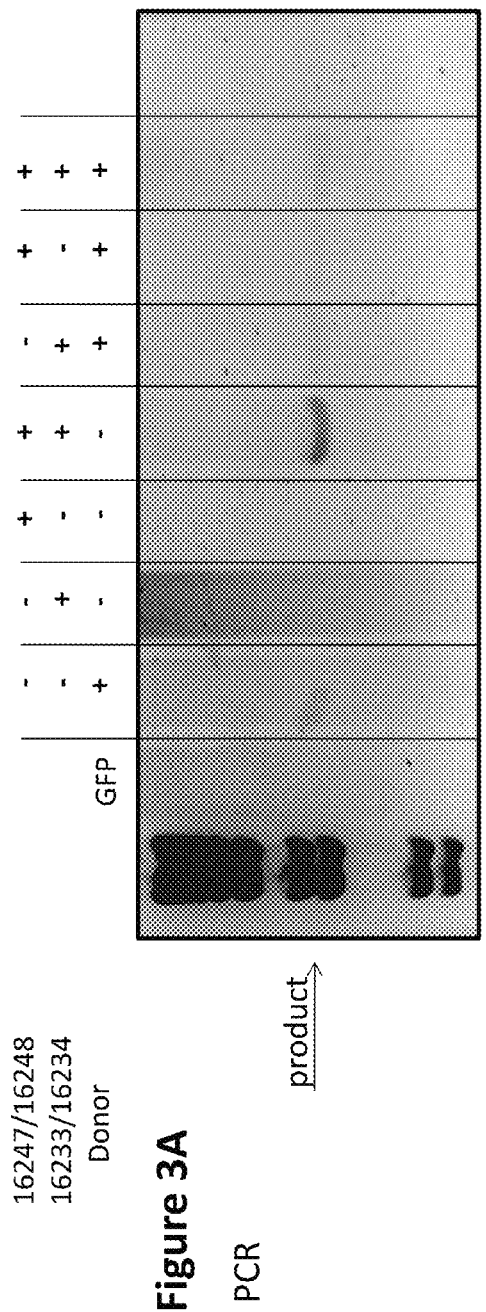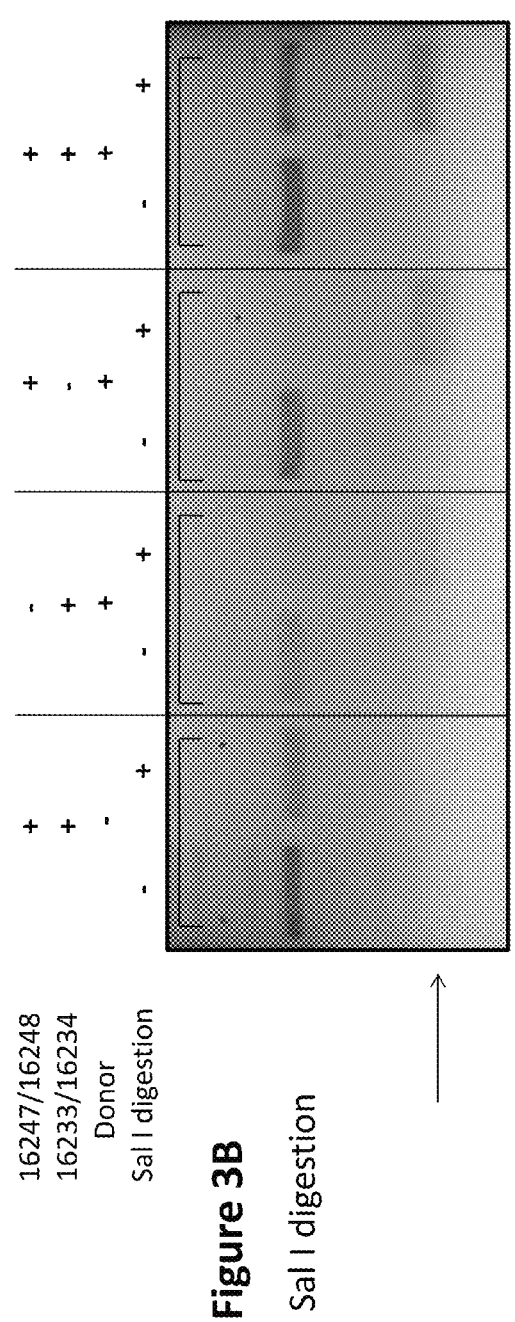
Figure 3A
PCR
Figure 3B
Sal I digestion

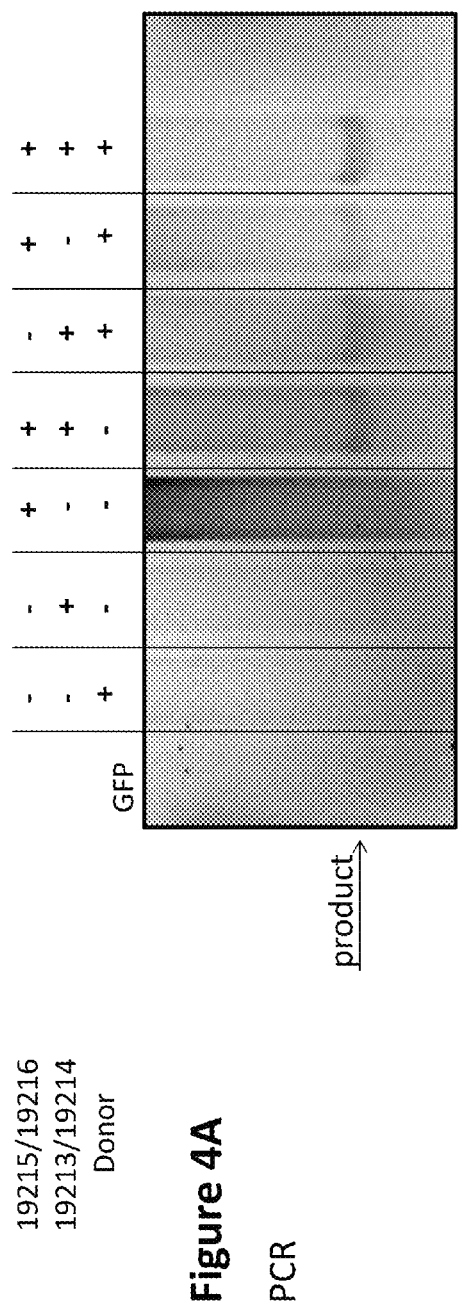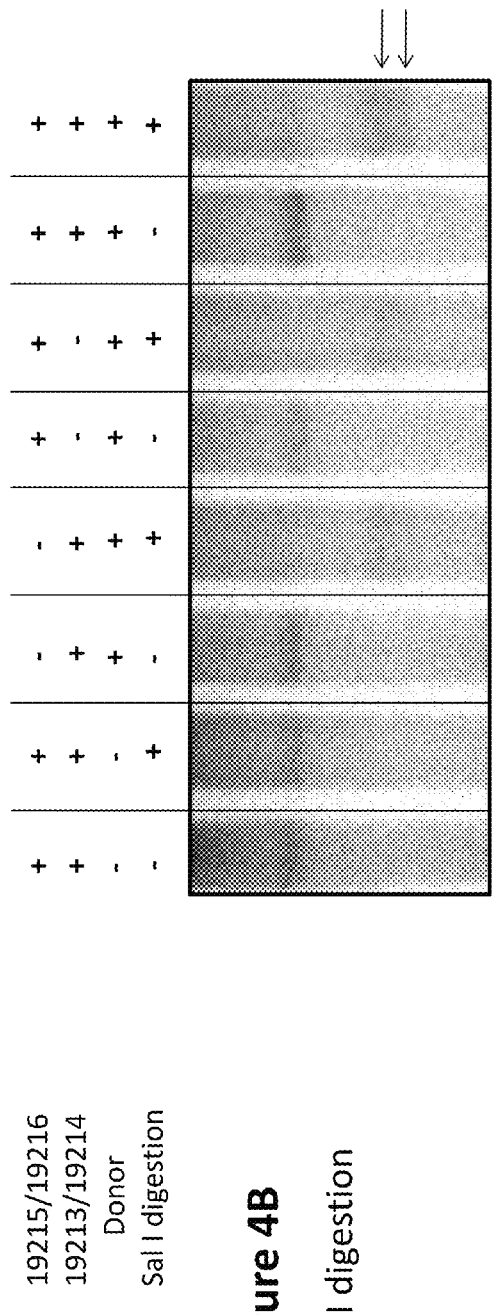
Figure 4A
PCR
Figure 4B
Sal I digestion

SEQUENCE LISTING

<160> NUMBER OF SEQ ID NOS: 76

<210> SEQ ID NO 1
<211> LENGTH: 16
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 1
ataaactgca aaaggc                                                      16

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Ser Asp Asn Leu Gly Val
1               5

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Lys Ile Asn Leu Gln Val
1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Ser Asp Val Leu Ser Glu
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gln Arg Asn His Arg Thr Thr
1               5

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aggatgagga tgacca                                                      16
```

```
<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Arg Ser Asn Leu Ser Arg
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Ser Ser Asn Leu Thr Ser
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ser Asp Asn Leu Ala Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Thr Ser Gly Asn Leu Thr Arg
1               5

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
gtcatctgct actcggga                                                 18

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12
```

Arg Ser Asp His Leu Ser Glu
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Arg Ser Thr Arg Thr Asn
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ser Ala Val Leu Ser Glu
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Asn Ser Asn Arg Ile Thr
1               5

<210> SEQ ID NO 16
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
atgacaagca gcggca                                                        16

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Ser Ala His Leu Ser Glu
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Arg Ser Ala Asn Leu Ser Glu
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Ser Ala Asn Leu Ser Val
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Arg Ala Asn Leu Ser Arg
1               5

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
atgtaacaaa ggactactct tcccccag                                            28

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Asn Ser Asp His Leu Thr Asn
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Arg Ser Asp Asn Leu Ser Val
1               5

<210> SEQ ID NO 24
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Asn Ala Thr Arg Ile Asn
1               5

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gln Ser Gly Ser Leu Thr Arg
1               5

<210> SEQ ID NO 26
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
atgagtcagt gaacagggaa tgggtgaa                                          28

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Arg Ser Asp His Leu Ser Ala
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Arg Ser Asn Arg Lys Thr
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ser Ala Ala Leu Ser Arg
1               5
```

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Ser Ala Asp Arg Thr Lys
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Arg Ser Ala Asn Leu Thr Arg
1               5

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
gccaggtctg ggcagctgca ggtgacca                                           28

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Ser Gly Asp Leu Thr Arg
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Ser Ser Asp Leu Arg Arg
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Glu Arg Gly Thr Leu Ala Arg
1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Arg Ser Asp His Leu Thr Thr
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Arg Ser Ala Leu Ser Arg
1               5

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Arg Ser Asp Asn Leu Arg Glu
1               5

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cccaggagag gagcaggcag ggtcagct                                         28

<210> SEQ ID NO 40
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Arg Ser His Leu Ser Arg
1               5

<210> SEQ ID NO 41
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 41

Gln Ser Gly His Leu Ser Arg
1               5

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Ser Ala Asn Leu Ala Arg
1               5

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
agtgagagca gtaggtgggc tgcctcag                                            28

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Arg Ser Asp Ser Leu Ser Ala
1               5

<210> SEQ ID NO 45
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Asn Asp Asn Arg Lys Thr
1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Ser Asp Asn Leu Ser Glu
1               5
```

```
<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Asn Ala His Arg Lys Thr
1               5

<210> SEQ ID NO 48
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
agggagttta tctggtaagg ggttccct                                           28

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Thr Ser Ser Asn Arg Lys Thr
1               5

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Thr Ser Gly Ser Leu Ser Arg
1               5

<210> SEQ ID NO 51
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
cgaaggtgtc cgaggcgccg gtcgtgcg                                           28

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Arg Ser Asp Thr Leu Ser Glu
```

```
<210> SEQ ID NO 53
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Ser Ala Asp Leu Ser Arg
1               5

<210> SEQ ID NO 54
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Ser Ser Asp Arg Lys Lys
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Leu Asp Asn Arg Thr Ala
1               5

<210> SEQ ID NO 56
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
gggttgggtg agtagcggtg accccttc                                          28

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ser Asp Asp Leu Thr Arg
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 58

Arg Ser Asp His Leu Ser Arg
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Thr Ser Gly Ser Leu Thr Arg
1               5

<210> SEQ ID NO 60
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
gggtagaagc ggtcacagat atatctgt                                      28

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gln Ser Gly Asn Leu Ala Arg
1               5

<210> SEQ ID NO 62
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
atgacttgtg ggtggttgtg ttccagtt                                      28

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Ser Asp Ser Leu Leu Arg
1               5

<210> SEQ ID NO 64
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 64

Asp Arg Ser Asn Leu Thr Arg
1               5

<210> SEQ ID NO 65
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ctgcctcata aggttgccct aag                                            23

<210> SEQ ID NO 66
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ccagcaatag atgatccaac tcaaattcc                                      29

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
aaagtttctg tgggggacct                                                20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
catcccactg agaaccactg                                                20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cagctgcttc ctggtttgaa                                                20

<210> SEQ ID NO 70
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 70
gatccaaggg cttctgcctt                                                      20

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
ccaagtgata aacacgagga tgg                                                  23

<210> SEQ ID NO 72
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ccagcatttc tataccactt tgg                                                  23

<210> SEQ ID NO 73
<211> LENGTH: 9
<212> TYPE: PRT
<213> ORGANISM: Unknown
<220> FEATURE:
<223> OTHER INFORMATION: Description of Unknown: "LAGLIDADG" motif
      peptide

<400> SEQUENCE: 73

Leu Ala Gly Leu Ile Asp Ala Asp Gly
1               5

<210> SEQ ID NO 74
<211> LENGTH: 29
<212> TYPE: DNA
<213> ORGANISM: Homo sapiens

<400> SEQUENCE: 74
gtcatcctca tcctgataaa ctgcaaaag                                            29

<210> SEQ ID NO 75
<211> LENGTH: 31
<212> TYPE: DNA
<213> ORGANISM: Homo sapiens

<400> SEQUENCE: 75
ccgctgcttg tcatggtcat ctgctactcg g                                         31

<210> SEQ ID NO 76
<211> LENGTH: 47
<212> TYPE: DNA
<213> ORGANISM: Homo sapiens

<400> SEQUENCE: 76
acatgctggt catcctcatc ggatccatct gctactcggg aatccta                        47
```

METHODS AND COMPOSTIONS FOR TARGETED GENOMIC DELETION

CROSS-REFERENCE TO RELATED APPLICATIONS

The present application is a continuation of U.S. application Ser. No. 14/502,773, filed Sep. 30, 2014, now U.S. Pat. No. 9,249,428, which is a continuation of Ser. No. 13/310,263, filed Dec. 2, 2011, which claims the benefit of U.S. Provisional Application No. 61/458,957, filed Dec. 3, 2010. U.S. patent application Ser. No. 14/502,773, now U.S. Pat. No. 9,249,428, is also a continuation-in-part of U.S. application Ser. No. 13/784,634 which is a continuation of U.S. patent application Ser. No. 11/304,981, filed Dec. 15, 2005, now U.S. Pat. No. 8,409,861, which is continuation-in-part of U.S. patent application Ser. No. 10/912,932, filed Aug. 6, 2004, now U.S. Pat. No. 7,888,121. U.S. patent application Ser. No. 11/304,981, now U.S. Pat. No. 8,409,861, claims the benefit of U.S. Provisional Application No. 60/649,515, filed February 2005, U.S. Patent Application Ser. No. 10/912,932. now U.S. Pat. No. 7,888,121 claims the benefit of the following U.S. provisional patent applications: 60/493,931 filed Aug. 8, 2003; 60/518,253 filed Nov. 7, 2003; 60/530,541 filed Dec. 18, 2003; 60/542,780 filed Feb. 5, 2004; 60/556,831 filed Mar. 26, 2004 and 60/575,919 filed Jun. 1, 2004. The disclosures of all of the above are hereby incorporated by reference in their entireties for all purposes.

TECHNICAL FIELD

The present disclosure is in the field of genome engineering, particularly methods and compositions for specific targeted deletions within the genome of a cell.

BACKGROUND

A major area of interest in genome biology, especially in light of the determination of the complete nucleotide sequences of a number of genomes, is the targeted manipulation of genomic sequences. Such targeted cleavage events can be used, for example, to induce targeted mutagenesis, induce targeted deletions of cellular DNA sequences, and facilitate targeted recombination at a predetermined chromosomal locus. See, for example, U.S. Pat. No. 7,888,121 and U.S. Patent Publications 20030232410; 20050208489; 20050026157; 20050064474; 20060188987; International Publication WO 2011/14612 (U.S. application Ser. No. 13/068,735) and International Publication WO 2007/014275, the disclosures of which are incorporated by reference in their entireties for all purposes. See, also, Santiago et al. (2008) *Proc Nat'l Acad Sci USA* 105:5809-5814; Perez et al. (2008) *Nat Biotechnol* 26:808-816 (2008).

Artificial nucleases, which link the cleavage domain of a nuclease to a designed DNA-binding protein (e.g., zinc-finger protein (ZFP) or transcription activator like effector (TALE) linked to a nuclease cleavage domain such as from FokI), have been used for targeted cleavage in eukaryotic cells. For example, nuclease-mediated genome editing has been shown to modify the sequence of the human genome at a specific location by (1) creation of a double-strand break (DSB) in the genome of a living cell specifically at the target site for the desired modification, and by (2) allowing the natural mechanisms of DNA repair to "heal" this break. See, for example, U.S. Pat. No. 7,888,121 and U.S. application Ser. No. 13/068,735, the disclosures of which are incorporated by reference in their entireties for all purposes as well as U.S. Patent Publication Nos. 2011/0145940 and 2011/0201118.

To increase specificity, the cleavage event is induced using one or more pairs of custom-designed zinc finger nucleases that dimerize upon binding DNA to form a catalytically active nuclease complex. In addition, specificity has been further increased by using one or more pairs of nucleases that include engineered cleavage half-domains that cleave double-stranded DNA only upon formation of a heterodimer. See, e.g., U.S. Patent Publication Nos. 20080131962; 20090305346 and 20110201055, incorporated by reference herein in their entireties.

The double-stranded breaks (DSBs) created by artificial nucleases have been used, for example, to induce targeted mutagenesis, induce targeted deletions of cellular DNA sequences, and facilitate targeted recombination at a predetermined chromosomal locus. See, for example, United States Patent Publications 20030232410; 20050208489; 20050026157; 20050064474; 20060188987; 20060063231; 20070218528; 20070134796; 20080015164 and International Publication Nos. WO 07/014275 and WO 2007/139982 and U.S. Ser. No. 13/068,735, the disclosures of which are incorporated by reference in their entireties for all purposes. Thus, the ability to generate a DSB at a target genomic location allows for genomic editing of any genome.

There are two major and distinct pathways to repair DSBs—homologous recombination and non-homologous end-joining (NHEJ). Homologous recombination requires the presence of a homologous sequence as a template (known as a "donor") to guide the cellular repair process and the results of the repair are error-free and predictable. In the absence of a template (or "donor") sequence for homologous recombination, the cell typically attempts to repair the DSB via the error-prone process of NHEJ.

Chromosomal translocations are chromosomal abnormalities wherein there is genetic rearrangement between non-homologous chromosomes. Found in 1 of every 625 newborns, these rearrangements are thought to be generally harmless but about 6% may play a role in human disease (see M. Oliver-Bonet; et al (October 2002). *Molecular Human Reproduction* 8 (10): 958-963, Brunet et al (2009) *Proc. Natl. Acad. Sci., USA* 106(26): 10620-10625). For example several cancers such as Burkitt's lymphoma, Mantle cell lymphoma, Follicular lymphoma, chronic myelogenous leukemia (CML), acute lymphoblastic leukemia (ALL) and others are known to be associated with chromosomal translocations. In the case of CML and ALL, one chromosomal translocation that has been associated with these two diseases is the production of the so-called Philadelphia chromosome, which is a result of a reciprocal translocation between chromosome 9 and 22 wherein the translocation is designated t(9;22)(q34;q11). This particular translocation causes the unregulated activity of a tyrosine kinase. The tyrosine kinase inhibitor imatinib has been shown to have specificity for this tyrosine kinase and has proven to be a valuable tool for the treatment of CML.

However, there remains a need for additional methods and exogenous polynucleotides for creating targeted deletions at specific locations within the genome where the targeted deletions can range from small (e.g. a few base pairs) to large (e.g. hundreds of thousands of nucleotides) that can be used in numerous models, diagnostic and therapeutic systems. Also, there remains the need for additional models of specific chromosomal translocations to further develop novel therapeutics to treat diseases associated with these chromosomal abnormalities.

SUMMARY

The present disclosure provides compositions and methods for creating deletions of specific size, at specific locations and with specific borders at a desired locus in a genome as well as method of creating specific chromosomal translocations. The methods rely on the use of targeted nucleases to cleave the DNA which can be combined with donor nucleotides with regions of homology ("homology arms") to the regions on the distal sides of the cleavage site within the targeted chromosome. Generally, the donor molecules described herein have two homology arms of between about 50 and 100 base pairs, but donors of greater homology (e.g., up to 1.5 kb each) can also be used.

The deletions, which can range in size from a few base pairs to hundreds of thousands of nucleotides (or any value therebetween) are created at a desired location in the genome, with desired borders (end points) for example using zinc finger nucleases (ZFNs), transcription activator like effector nucleases (TALENs) and/or meganucleases, optionally in combination with an exogenous "donor" sequence. The optional provision of an exogenous nucleic acid donor sequence which is integrated following targeted double-strand cleavage of the genome (chromosome) in the region of interest can facilitate delineation of end points (borders) of the deletion. Similarly, the translocations can range in size from a few base pairs to thousands or nucleotides (or any value therebetween).

Thus, in one aspect, described herein are exogenous (donor) polynucleotides for targeted integration into a genome. The donors described herein comprise a deletion of specified length and with specified borders as compared to the endogenous sequence into which the donor is integrated. In certain embodiments, the donor molecule includes one or more regions (sequences) of homology to the endogenous target, for example a region of homology on one side of the deletion site or two regions of homology surrounding the deletion site. Any of the donor molecules described herein may include one, two or more sites recognized by one or more nucleases (e.g., one or more zinc finger nucleases, one or more meganucleases, one or more TALENs and/or one or more restriction endonucleases).

In other aspects, described herein are methods of cleaving endogenous targets such that deletions of defined borders and length are created in an endogenous genome. In certain embodiments, cleavage is targeted to the region of interest through the use of fusion proteins comprising a zinc finger or TALE DNA binding domain, which has been engineered to bind a sequence within the region of interest, and a cleavage domain or a cleavage half-domain. In other embodiments, one or more pairs of zinc finger nucleases (ZFNs) and/or TALENs are used to cause at least one double strand break. In certain embodiments, cleavage is achieved using two pairs of nucleases to induce two double strand breaks.

In a further aspect, the methods and compositions of the invention are used to create a translocation event, where a novel chromosome is made by inducing a double strand break on one chromosome, inducing a second double strand break on a second chromosome, and using a donor molecule containing arms that are homologous to each desired chromosomal fragment such that the two desired chromosomal fragments are joined and a novel translocated chromosome is produced.

In one aspect, targeted deletions as described herein are made using a linear nucleic acid molecule (donor molecule) comprising homology arms of 50-100 base pairs flanking the cleavage site of interest is provided. In certain embodiments, when two double strand breaks are induced, the donor molecule contains arms that are homologous with the regions of the cleaved genome on the exterior or distal side of the deletion site. In certain embodiments, the donor molecule stably persists in the cell into which it is introduced. In some embodiments, the donor molecule further comprises a sequence of interest between the homology arms. In other embodiments, the linear donor molecule is modified to resist exonucleolytic cleavage, for example by placing one or more phosphorothioate phosphodiester bonds between one or more base pairs on the ends of the donor molecule. In some embodiments, the donor is present on a plasmid. In certain embodiments, the targeted deletions as described herein at made using a donor molecule with homology arms comprising up to 1500 bp of homology flanking the cleavage site of interest.

The sequence of interest of the donor molecule may comprise one or more sequences encoding a functional polypeptide (e.g., a cDNA) or fragment thereof, with or without a promoter. In certain embodiments, the nucleic acid sequence comprises a promoterless sequence encoding an antibody, an antigen, an enzyme, a growth factor, a receptor (cell surface or nuclear), a hormone, a lymphokine, a cytokine, a reporter, functional fragments of any of the above and combinations of the above. Expression of the integrated sequence is then ensured by transcription driven by an endogenous promoter or other control element in the region of interest. In other embodiments, a "tandem" cassette is integrated into the selected site in this manner, the first component of the cassette comprising a promoterless sequence as described above, followed by a transcription termination sequence, and a second sequence, encoding an autonomous expression cassette. Additional sequences (coding or non-coding sequences) may be included in the donor molecule between the homology arms, including but not limited to, sequences encoding a 2A peptide, SA site, IRES, etc. Donor molecules may also comprise a nucleic acid encoding a RNA molecule which as a shRNA, miRNA or RNAi and the like. Donor molecules may further comprise sequences encoding a RNA molecule and those encoding a function polypeptide or fragment thereof.

The donor molecules of the disclosure can be inserted into a specified location in a genome following cleavage of the genome, for example using one or more fusion molecules comprising a DNA-binding domain targeted to the specified location in the genome and a cleavage domain (e.g., a zinc finger nuclease (ZFN), a TALEN and/or a naturally or non-naturally occurring meganuclease to a particular locus).

Thus, in another aspect, provided herein is a method for integrating an exogenous sequence as described herein into a deletion in the region of interest in the genome of a cell, the method comprising: (a) expressing a fusion protein in the cell, the fusion protein comprising a DNA-binding domain (e.g., zinc finger-, or TALE-DNA binding domain) and a cleavage domain or cleavage half-domain, wherein the DNA-binding domain (e.g., zinc finger or TALE DNA binding domain) has been engineered to bind to a target site in the region of interest in the genome of the cell; and (b) contacting the cell with a donor polynucleotide as described herein, wherein binding of the fusion protein to the target site cleaves the genome of the cell in the region of interest, thereby resulting in a targeted deletion and followed by the integration of the exogenous sequence into the genome of the cell within the targeted deletion of a desired size in the region of interest. In certain embodiments, the targeted deletion recapitulates a known structural variant at the target locus.

In certain embodiments, the methods comprise the steps of (a) expressing a first fusion protein in the cell, the first fusion protein comprising a first zinc finger- or TALE-DNA binding domain and a first cleavage half-domain, wherein the first zinc finger- or TALE-DNA binding domain has been engineered to bind to a first target site in the region of interest in the genome of the cell; (b) expressing a second fusion protein in the cell, the second fusion protein comprising a second zinc finger- or TALE-DNA binding domain and a second cleavage half domain, wherein the second zinc finger- or TALE-DNA binding domain binds to a second target site in the region of interest in the genome of the cell, wherein the second target site is different from the first target site; and (c) contacting the cell with a exogenous donor molecule as described herein, wherein binding of the first fusion protein to the first target site, and binding of the second fusion protein to the second target site, positions the cleavage half-domains such that the genome of the cell is cleaved in the region of interest, thereby resulting in a targeted deletion and integration of the exogenous donor molecule into the genome of the cell within the region of interest.

In any of the methods described herein, the donor polynucleotide comprises a sequence encoding a functional polypeptide or RNA, which sequence is inserted into the genome of the cell at the site of the targeted deletion.

Furthermore, in any of the methods described herein, the first and second cleavage half-domains are from a Type IIS restriction endonuclease, for example, FokI or StsI. Furthermore, in any of the methods described herein, at least one of the fusion proteins may comprise an engineered cleavage domain or cleavage half-domain which includes alteration in the amino acid sequence of the dimerization interface of the cleavage half-domain, for example such that obligate heterodimers of the cleavage half-domains are formed. Alternatively, in any of the methods described herein the cleavage domain may be a naturally or non-naturally occurring meganuclease.

In any of the methods described herein, the cell can be a mammalian cell, for example, a human cell. Furthermore, the cell may be arrested in the G2 phase of the cell cycle. In addition, the invention includes host cells, cell lines and transgenic organisms (e.g., plants, animals) comprising these proteins/polynucleotides and/or modified by these proteins (e.g., genomic modification that is passed onto the progeny). Exemplary cells and cell lines include animal cells (e.g., mammalian, including human, cells such as stem cells), plant cells, bacterial cells, protozoal cells, fish cells, or fungal cells.

In another aspect, described herein is a host cell comprising one or more donor DNAs as described herein and one or more ZFP- and/or TALE-fusion protein expression vectors as described herein. The host cell may be stably transformed or transiently transfected or a combination thereof with one or more of these protein expression vectors. In one embodiment, the host cell is an embryonic stem cell. In other embodiments, the one or more protein expression vectors express one or fusion proteins in the host cell. In another embodiment, the host cell may further comprise an exogenous polynucleotide donor sequence. In any of the embodiments, described herein, the host cell may comprise a stem cell. The stem cell may be a mammalian stem cell, for example, a hematopoietic stem cell, a mesenchymal stem cell, an embryonic stem cell, a neuronal stem cell, a muscle stem cell, a liver stem cell, a skin stem cell, an induced pluripotent stem cell and/or combinations thereof. In certain embodiments, the stem cell is a human induced pluripotent stem cells (hiPSC) or a human embryonic stem cell (heSC). In any of the embodiments, described herein, the host cell can comprise an embryo cell, for example a one or more mouse, rat, rabbit or other mammal cell embryo. In some aspects, stem cells or embryo cells are used in the development of transgenic animals. In further aspects, these transgenic animals are used for research purposes, i.e. mice, rats, rabbits; while in other aspects, the transgenic animals are livestock animals, i.e. cows, chickens, pigs, sheep etc. In still further aspects, the transgenic animals are those used for therapeutic purposes, i.e. goats, cows, pigs; and in other aspects, the transgenic animals are companion animals, i.e. cats, dogs, horses, birds or fish. In other embodiments, the host cell is a fibroblast. In some embodiments, the host cell is a plant cell. In other aspects, the host cell is part of a plant tissue such as the vegetative parts of the plant, storage organs, fruit, flower and/or seed tissues. In further embodiments, the host cell is an algae cell.

In yet a further aspect, provided herein are kits comprising the donors as described herein and optionally one or more nucleases (e.g., ZFNs and/or TALENs). These kits may be used to facilitate the introduction of targeted deletions of specified length and boundaries and/or for creation of novel chromosomal translocations, for example by providing a ZFN or TALEN that will result in a targeted deletion in a desired target or a safe harbor locus within a genome. The ZFN or TALEN may be provided either as nucleic acid (e.g. DNA or RNA) or may be provided as protein. In some instances, the protein may be formulated to increase stability, or may be provided in a dried form.

BRIEF DESCRIPTION OF THE DRAWINGS

FIG. 1A is a cartoon showing the target DNA and a donor molecule. The location of the ZFN binding sites as well as the location of the PCR primers used for analyzing the cleavage products are indicated. FIG. 1B shows the sequence around the two ZFN target sites (160 and 630) in the human CCR5 gene (SEQ ID NOS 74 and 75, respectively, in order of appearance). Binding sites for the two ZFN pairs are indicated on the top of the figure in the target site, and the donor to be used is shown below in FIG. 1C (SEQ ID NO: 76). The donor contains a unique BamHI site for identification of insertion following cleavage with the ZFNs.

FIGS. 3A and 3B depict results of targeted deletion at the POUF1 locus. FIG. 3A is a gel depicting the PCR amplification product while FIG. 3B depicts results following cleavage of the PCR product with the Sal I restriction enzyme. Experimental constituents (+/−ZFNs and/or donor) are indicated above the lanes. A unique Sal I site was present in the donor molecule, and integration of the donor would result in a Sal I cleavable PCR product in this experiment. Since it is possible to close (repair) the DSB following cleavage by both the nucleases using NHEJ without the incorporation of the donor, the PCR product is evident in the lower gel in the sample lacking a donor. But, as is apparent from the gel shown in the FIG. 3B), this PCR product is not cleavable by Sal I. When only one nuclease pair is used, the presence of a donor results in a PCR product that is almost completely digested by the Sal I enzyme. NHEJ may occur in this sample as well, but the size of the resultant products may be highly variable, and thus will not produce a specific PCR product using the designed primers.

FIGS. 4A and 4B are reproductions of gels depicting results of targeted deletion of >120 Kb. FIG. 4A shows the PCR product that spans the healed cleavage locations, while FIG. 4B shows results of Sal I digestion of that PCR product. Experimental constituents and conditions (+/−ZFNs and/or donor, +/−Sal I digestion are shown above the lanes) As can be seen from FIG. 4B, when both ZFN pairs are present and a donor is used, the donor can get inserted and thus the PCR product is cleavable by Sal I. Sal I cleavage products are indicated by arrows in FIG. 4B.

FIG. 5 also depicts a schematic of the patch donor used in this experiment.

DETAILED DESCRIPTION

Figure 1:
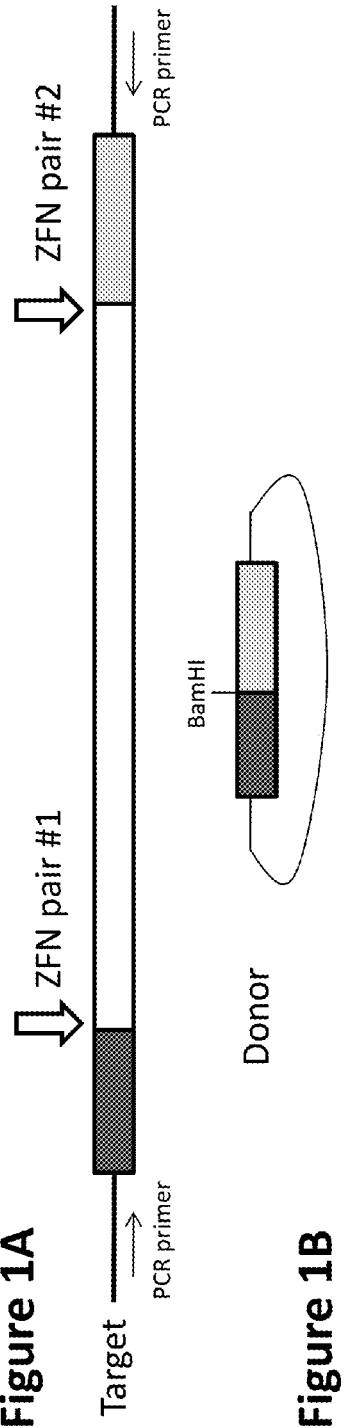
FIGS. 1A through 1C are schematic diagrams depicting construction of a linear donor polynucleotide as described herein.

The present invention relates to methods and compositions to create deletions of defined lengths at specific sites within a genome and to methods of creating novel translocations. The deletions may span a few nucleotides or may cause the loss of up to hundreds of thousands of nucleotides. These targeted, specific deletions are useful in a variety of genetic remodeling and targeted manipulation applications, as well as for the controlled creation of specific chromosomal translocations. The present disclosure also relates to exogenous (donor) polynucleotides useful for homology-dependent targeted deletions (TD) and/or targeted integration (TI) into a region of interest in a genome. Any donor polynucleotide can be used including plasmid donors or linear donors. Preferably, donor polynucleotides include homology arms exhibiting homology to the region of interest. In certain embodiments, the donor polynucleotides are linear molecules comprising homology arms (HA) of approximately 50-100 base pairs while in other embodiments, homology arms may comprise sequences up to 1500 bp in length. The homology arms flank one or more sequences of interest to be inserted into the genome of a cell. These donor molecules are useful for targeted cleavage and recombination into a specified region of interest in a genome when used in combination with fusion proteins (zinc finger- or TALE-nucleases) comprising a cleavage domain (or a cleavage half-domain) and a zinc finger or TALE DNA binding domain (and/or polynucleotides encoding these proteins). A zinc finger binding domain can comprise one or more zinc fingers (e.g., 2, 3, 4, 5, 6, 7, 8, 9 or more zinc fingers), and can be engineered to bind to any sequence within the region of interest. A TALE DNA binding domain may comprise up to 40 or 50 repeat units, and may be engineered to bind to any sequence within a region of interest. In the presence of ZFNs and/or TALENs, the linear donor polynucleotides described are integrated at high rates into the cleavage site(s) and the donors can be used to guide precise rejoining of cleaved DNA ends.

Advantages to the methods and materials described herein include the ability for the user to generate deletions of specific lengths at sites of their choosing with exact borders, and to have those deletions encompass small or very large stretches of the genome. Furthermore, the present invention provides methods for making precise chromosome translocations and thus may be used to develop model systems for diseases at levels of precision not previously available. Additionally, the invention provides methods and compositions for the insertion of specific sequences within the deleted region if desired by the user.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, also, U.S. patent application Ser. No. 13/068,735.

Zinc finger binding domains can be "engineered" to bind to a predetermined nucleotide sequence, for example via engineering (altering one or more amino acids) of the recognition helix region of a naturally occurring zinc finger protein. Similarly, TALEs can be "engineered" to bind to a predetermined nucleotide sequence, for example by engineering of the amino acids involved in DNA binding (the RVD region). Therefore, engineered zinc finger proteins or TALE proteins are proteins that are non-naturally occurring. Non-limiting examples of methods for engineering zinc finger proteins and TALEs are design and selection. A designed protein is a protein not occurring in nature whose design/composition results principally from rational criteria. Rational criteria for design include application of substitution rules and computerized algorithms for processing information in a database storing information of existing ZFP or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. application Ser. No. 13/068,735

A "selected" zinc finger protein or TALE is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084 and U.S. patent application Ser. No. 13/068,735.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger and/or additional TALEN proteins can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or non-coding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miR-NAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 20050064474, 20070218528, 20080131962, and 20110201055 incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylates, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

A chromosomal "translocation" is a chromosome abnormality caused by rearrangement of segments between different (nonhomologous) chromosomes. A gene fusion may be created when the translocation joins two separate genes (e.g., as seen in some cancers). Translocations may be "reciprocal" (also known as non-Robertsonian), in which non-homologous chromosomes exchange genetic material. Alternatively, translocations may be "Robertsonian," in which two acrocentric chromosomes fuse near the centromere region with loss of the short arms. The International System for Human Cytogenetic Nomenclature (ISCN) is used to denote a translocation between chromosomes as follows: t(A;B)(p1;q2), wherein "t" refers to a translocation between chromosome A and chromosome B. The information in the second set of parentheses, when given, gives the precise location within the chromosome for chromosomes A and B respectively—with p indicating the short arm of the chromosome, q indicating the long arm, and the numbers after p or q refers to regions, bands and subbands seen when staining the chromosome with a staining dye.

Targeted Deletion

Using the methods described herein, deletions of specific lengths and at specific locations can be made at any desired locus of a genome. The methods involve inducing at least one double stranded break (DSB), typically using a nuclease (e.g., ZFN or TALEN), which the nuclease is targeted to a specific location in the genome. The nuclease(s) cleave at the specific target sites and can thereby induce deletions. Cells with the desired targeted deletions can be readily selected.

In certain embodiments, targeted deletion is facilitated by integration of a donor polynucleotide, which can aid in defining the length and borders of the desired deletion. By "integration" is meant both physical insertion (e.g., into the genome of a host cell) and, in addition, integration by copying of the donor sequence into the host cell genome via the nucleic acid replication processes.

For targeted deletion via integration of a donor sequence, one or more zinc finger and/or TALE DNA binding domains are engineered to bind a target site at or near the predetermined cleavage site, and a fusion protein comprising the engineered zinc finger or TALE DNA binding domain and a cleavage domain is expressed in a cell. Upon binding of the DNA binding domain portion of the fusion protein to the target site, the DNA is cleaved, preferably via a double stranded break, near the target site by the cleavage domain. The presence of a double-stranded break facilitates integration of exogenous sequences as described herein via homologous recombination. In certain embodiments, a single DSB is introduced by the nuclease, which enhances integration of the donor polynucleotide to create the targeted deletion. In other embodiments, two or more DSBs are introduced by the nuclease(s).

Targeted integration of exogenous sequences, as disclosed herein, can be used to generate cells and cell lines for protein expression. See, for example, co-owned U.S. Patent Application Publication No. 2006/0063231 (the disclosure of which is hereby incorporated by reference herein, in its entirety, for all purposes). For optimal expression of one or more proteins encoded by exogenous sequences integrated into a genome, the chromosomal integration site should be compatible with high-level transcription of the integrated sequences, preferably in a wide range of cell types and developmental states. However, it has been observed that transcription of integrated sequences varies depending on the integration site due to, among other things, the chromatin structure of the genome at the integration site. Accordingly, genomic target sites that support high-level transcription of integrated sequences are desirable. In certain embodiments, it will also be desirable that integration of exogenous sequences not result in ectopic activation of one or more cellular genes (e.g., oncogenes). On the other hand, in the case of integration of promoter and/or enhancer sequences, ectopic expression may be desired.

Nucleases

Described herein are methods involving and compositions comprising, nucleases which cleave double-stranded DNA. In certain embodiments, the nuclease is naturally occurring. In other embodiments, the nuclease is non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector nucleases; meganuclease DNA-binding domains with heterologous cleavage domains).

A. DNA-Binding Domains

In certain embodiments, the nuclease is a meganuclease (homing endonuclease). Naturally-occurring meganucleases recognize 15-40 base-pair cleavage sites and are commonly grouped into four families: the LAGLIDADG family ("LAGLIDADG" disclosed as SEQ ID NO: 73), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

In certain embodiments, the nuclease comprises an engineered (non-naturally occurring) homing endonuclease (meganuclease). The recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain comprises a naturally occurring or engineered (non-naturally occurring) TAL effector DNA binding domain. See, e.g., U.S. patent application Ser. No. 13/068,735, incorporated by reference in its entirety herein. The plant pathogenic bacteria of the genus *Xanthomonas* are known to cause many diseases in important crop plants. Pathogenicity of *Xanthomonas* depends on a conserved type III secretion (T3 S) system which injects more than 25 different effector proteins into the plant cell. Among these injected proteins are transcription activator-like effectors (TALE) which mimic plant transcriptional activators and manipulate the plant transcriptome (see Kay et at (2007) *Science* 318:648-651). These proteins contain a DNA binding domain and a transcriptional activation domain. One of the most well characterized TALEs is AvrBs3 from *Xanthomonas campestgris* pv. *Vesicatoria* (see Bonas et al (1989) *Mol Gen Genet* 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et at (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

In other embodiments, the DNA-binding domain comprises a zinc finger binding domain, for example an engineered (non-naturally occurring) zinc finger binding domain. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, DNA domains (e.g., multi-fingered zinc finger proteins or TALEs) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The zinc finger proteins described herein may include any combination of suitable linkers between the individual zinc fingers of the protein. In addition, enhancement of binding specificity for zinc finger binding domains has been described, for example, in co-owned WO 02/077227.

Selection of target sites; DNA-binding domains and methods for design and construction of fusion proteins (and polynucleotides encoding same) are known to those of skill in the art and described in detail in U.S. Pat. Nos. 6,140, 0815; 789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, DNA binding domains (e.g., multi-fingered zinc finger proteins, TALEs) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Nat'l Acad Sci USA* 93(3):1156-1160. More recently, ZFNs have been used for genome modification in a variety of organisms. See, for example, United States Patent Publications 20030232410; 20050208489; 20050026157; 20050064474; 20060188987; 20060063231; and International Publication WO 07/014275. Similarly, TALE DNA-binding domains can be linked to nuclease domains to create TALENs. See, e.g., U.S. Ser. No. 13/068,735.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains. See, also, U.S. Patent Publication Nos. 20050064474, 20070218528, 20080131962, and 20110201055

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes.

In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See U.S. application Ser. No. 12/931,660). In still further embodiments, the engineered cleavage half domains comprise mutations such that a nuclease pair is made with one H537R-R487D-N496D ("RDD") FokI half domain and one N496D-D483R-H537R ("DRR") FokI half domain.

Engineered cleavage half-domains described herein can be prepared using any suitable method, for example, by site-directed mutagenesis of wild-type cleavage half-domains (Fok I) as described in U.S. Patent Publication Nos. 20050064474 and 20080131962.

Alternatively, nucleases may be assembled in vivo at the nucleic acid target site using so-called "split-enzyme" technology (see e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Nuclease expression constructs can be readily designed using methods known in the art. See, e.g., United States Patent Publications 20030232410; 20050208489; 20050026157; 20050064474; 20060188987; 20060063231; and International Publication WO 07/014275. Expression of the nuclease may be under the control of a constitutive promoter or an inducible promoter, for example the galactokinase promoter which is activated (de-repressed) in the presence of raffinose and/or galactose and repressed in presence of glucose.

Target Sites

As described in detail above, DNA domains can be engineered to bind to any sequence of choice in a locus. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual (e.g., zinc finger) amino acid sequences, in which each triplet or quadruplet nucleotide sequence is associated with one or more amino acid sequences of DNA binding domain which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. patent application Ser. No. 13/068,735.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Provisional Patent Application No. 61/343,729.

Donors

As noted above, insertion of an exogenous sequence (also called a "donor sequence" or "donor" or "transgene") can facilitate making deletions of the desired size and borders. A donor sequence can contain a non-homologous sequence (e.g., including the deletion) flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA, single-stranded or double-stranded and can be introduced into a cell in linear or circular form. In addition, a donor polynucleotide may be a single or double stranded oligonucleotide. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues. See, also, U.S. Patent Publication No. 20110207221.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or a macromolecule such as a dendrimir (See Wijagkanalen et at (2011) *Pharm Res* 28(7) p. 1500-19), or can be delivered by viruses (e.g., adenovirus, helper-dependent adenovirus, AAV, herpesvirus, retrovirus, lentivirus and integrase defective lentivirus (IDLV)).

Applications

The disclosed methods and compositions can be used for genomic editing of any gene or genes. In certain applications, the methods and compositions can be used for inactivation of genomic sequences. To date, cleavage-based methods have been used to target modifications to the genomes of at least nine higher eukaryotes for which such capabilities were previously unavailable, including economically (agriculturally and medically) important species such as corn, mouse and rat.

In other applications, the methods and compositions allow for generation of novel mutations (targeted deletions of defined, known size and location and/or translocations), including generation of novel allelic forms of genes with different expression or biological properties as compared to unedited genes or integration of humanized genes, which in turn allows for the generation of cell or animal models. In other applications, the methods and compositions can be used for creating random mutations at defined positions of genes that allows for the identification or selection of animals carrying novel allelic forms (e.g., translocations) of those genes. In other applications, the methods and compositions allow for targeted integration of an exogenous (donor) sequence into any selected area of the genome. Regulatory sequences (e.g. promoters) could be integrated in a targeted fashion at a site of interest. By "integration" is meant both physical insertion (e.g., into the genome of a host cell) and, in addition, integration by copying of the donor sequence into the host cell genome via the specialized nucleic acid information exchange process that occurs during homology-directed DNA repair.

Donor sequences for integration can also comprise nucleic acids such as shRNAs, miRNAs etc. These small nucleic acid donors can be used to study their effects on genes of interest within the genome. Genomic editing (e.g., inactivation, integration and/or targeted or random mutation) of an animal gene can be achieved, for example, by a single cleavage event, by cleavage followed by non-homologous end joining, by cleavage followed by homology-directed repair mechanisms, by cleavage followed by physical integration of a donor sequence, by cleavage at two sites followed by joining so as to delete the sequence between the two cleavage sites, by targeted recombination of a missense or nonsense codon into the coding region, by targeted recombination of an irrelevant sequence (i.e., a "stuffer" sequence) into the gene or its regulatory region, so as to disrupt the gene or regulatory region, or by targeting recombination of a splice acceptor sequence into an intron to cause mis-splicing of the transcript. In some applications, transgenes of interest may be integrated into a safe harbor locus within a mammalian or plant genome using ZFN- or TALEN-induced DSB at a specified location. See, U.S. Patent Publication Nos. 20030232410; 20050208489; 20050026157; 20050064474; 20060188987; 20060063231; and International Publication WO 07/014275, the disclosures of which are incorporated by reference in their entireties for all purposes. These ZFNs or TALENs may also be supplied as components of kits including donors for targeted genetic manipulation.

ZFP or TALE fusions may be useful in manufacturing settings. ZFNs or TALENs may be used in cell lines of interest (e.g. CHO cells) or in algae (e.g. for biofuel production).

There are a variety of applications for ZFP or TALE fusion proteins mediated genomic editing of a gene or genomic loci. The methods and compositions described herein allow for the generation of models of human diseases and for plant crops with desired characteristics.

The methods and compositions described herein can be used to create artificially translocated chromosomes. These translocations may be created in isolated cells, or may be constructed in embryonic stem cells for the development of transgenic animal models containing specific chromosomal translocation products. The specificity of cutting by the nucleases of the invention, combined with the ability to design the exact donor for insertion allows modeling of cells and organisms comprising chromosomal translocations known to be associated with human disease. Thus these models may also be used as screening tools to identify therapeutic agents capable of modifying the disease at a molecular level, influencing its presentation and associated sequelae.

Non-limiting examples of diseases associated with chromosomal translocations include infertility, Down Syndrome, mental illness such as schizophrenia (e.g., t(1;11)(q42.1; q14.3)) and various cancers such as breast cancers, Burkitt's lymphoma (e.g., cmyc/IGH; t(8;14)(q24;q32)); Mantle cell lymphoma (e.g., cyclin/IGH; t(11;14)(q13;q32)); follicular lymphoma (e.g., IGH/bcl-2; t(14;18)(q32;q21)); Papillary thyroid cancer (e.g., RET/PTC; t(10;(various))(q11;(various))); Follicular thyroid cancer (PAX8/PPARγ1; t(2;3)(q13; p25)); Acute myeloblastic leukemia with maturation (ETO/ AML; t(8;21)(q22;q22)); Chronic myelogenous leukemia (CML) or acute lymphoblastic leukemia (ALL) (e.g., t(9; 22)(q34;q11) the "Philadelphia chromosome" or JAK/TEL; t(9;12)(p24;p13) or TLE/AML; t(12;21)(p12;q22)); Acute promyelocytic leukemia (e.g., PML/RARα; t(15;17)); MALT lymphoma (e.g., t(11;18)(q21;q21)); Anaplastic large cell lymphoma (e.g., t(2;5)(p23;q35)); Ewing's sarcoma (t(11;22)(q24;q11.2-12)); dermatofibrosarcoma protuberans (DFSP) (e.g., t(17;22)); acute myelogenous leukemia (e.g., t(1;12)(q21;p13)); synovial sarcoma (e.g., t(X;18)(p11.2; q11.2)); and oligodendroglioma or oligoastrocytoma (e.g., t(1;19)(q10;p10)).

The compositions and methods described herein can also be used in the production of biofuels. Algae are being increasingly utilized for manufacturing compounds of interest, i.e. biofuels, plastics, hydrocarbons etc. Thus, the methods described herein can be used to generate algae with the desired characteristics as biofuels. Exemplary algae species include microalgae including diatoms and cyanobacteria as well as *Botryococcus braunii, Chlorella, Dunaliella tertiolecta, Gracileria, Pleurochrysis carterae, Sorgassum* and *Ulva*.

EXAMPLES

Example 1

Design, Construction and General Characterization of Zinc Finger Protein Nucleases (ZFN)

Zinc finger proteins were designed and incorporated into plasmids or adenoviral vectors essentially as described in Urnov et al. (2005) *Nature* 435(7042):646-651, Perez et at (2008) *Nature Biotechnology* 26(7):808-816, and as described in U.S. Pat. No. 6,534,261. Table 1 shows the recognition helices DNA binding domain of exemplary ZFPs and the target sites for these ZFPs. Nucleotides in the target site that are contacted by the ZFP recognition helices are indicated in uppercase letters; non-contacted nucleotides indicated in lowercase. Additionally, see United States Patent Application No: 20080159996 for CCR5-specific ZFNs, WO2010117464 for POU5F1-specific ZFNs and WO2010107493 for CXCR4-specific ZFNs.

TABLE 1

Zinc-finger Designs

| ZFN Name locus Target sequence | F1 | F2 | F3 | F4 | F5 | F6 |
|---|---|---|---|---|---|---|
| 8196 CCR5- atAAACTGCAAA AGgc (SEQ ID NO: 1) | RSDNLGV (SEQ ID NO: 2) | QKINLQV (SEQ ID NO: 3) | RSDVLSE (SEQ ID NO: 4) | QRNHRTT (SEQ ID NO: 5) | N/A | N/A |
| 8267 CCR5- agGATGAGGAT GACca (SEQ ID NO: 6) | DRSNLSR (SEQ ID NO: 7) | VSSNLTS (SEQ ID NO: 8) | RSDNLAR (SEQ ID NO: 9) | TSGNLTR (SEQ ID NO: 10) | N/A | N/A |
| 7645 CCR5- gtCATCTGctACT CGGga (SEQ ID NO: 11) | RSDHLSE (SEQ ID NO: 12) | ARSTRTN (SEQ ID NO: 13) | RSAVLSE (SEQ ID NO: 14) | TNSNRIT (SEQ ID NO: 15) | N/A | N/A |
| 7524 CCR5- atGACAAGCAGC GGca (SEQ ID NO: 16) | RSAHLSE (SEQ ID NO: 17) | RSANLSE (SEQ ID NO: 18) | RSANLSV (SEQ ID NO: 19) | DRANLSR (SEQ ID NO: 20) | N/A | N/A |
| 16247 POU5F1- atGTAACAAAGG ACTACtcttccccca g (SEQ ID NO: 21) | NSDHLTN (SEQ ID NO: 22) | DRANLSR (SEQ ID NO: 20) | RSDNLSV (SEQ ID NO: 23) | QNATRIN (SEQ ID NO: 24) | QSGSLTR (SEQ ID NO: 25) | N/A |
| 16248 POU5F1- atGAGTCAGTGA ACAGGgaatgggtg aa (SEQ ID NO: 26) | RSDHLSA (SEQ ID NO: 27) | DRSNRKT (SEQ ID NO: 28) | RSAALSR (SEQ ID NO: 29) | QSADRTK (SEQ ID NO: 30) | RSANLTR (SEQ ID NO: 31) | N/A |
| 16233 POU5F1- gcCAGGTCTGG GCAGCTGCAggt gacca (SEQ ID NO: 32) | QSGDLTR (SEQ ID NO: 33) | QSSDLRR (SEQ ID NO: 34) | ERGTLAR (SEQ ID NO: 35) | RSDHLTT (SEQ ID NO: 36) | DRSALSR (SEQ ID NO: 37) | RSDNLRE (SEQ ID NO: 38) |
| 16234 POU5F1- ccCAGGAGaGG AGCAGGCagggtc agct (SEQ ID NO: 39) | DRSHLSR (SEQ ID NO: 40) | QSGDLTR (SEQ ID NO: 33) | QSGHLSR (SEQ ID NO: 41) | RSANLAR (SEQ ID NO: 42) | RSDNLRE (SEQ ID NO: 38) | N/A |
| 19215 PRKCH- agTGAGAGCAG TAGGTGgctgcct cag (SEQ ID NO: 43) | RSDSLSA (SEQ ID NO: 44) | RNDNRKT (SEQ ID NO: 45) | RSDNLSE (SEQ ID NO: 46) | RSANLTR (SEQ ID NO: 31) | QNAHRKT (SEQ ID NO: 47) | N/A |

TABLE 1-continued

Zinc-finger Designs

| ZFN Name locus Target sequence | F1 | F2 | F3 | F4 | F5 | F6 |
|---|---|---|---|---|---|---|
| 19216 PRKCH- agGGAGTTTATC TGGTAAGGggttc cct (SEQ ID NO: 48) | RSDHLSA (SEQ ID NO: 27) | QSGSLTR (SEQ ID NO: 25) | RSDVLSE (SEQ ID NO: 4) | TSSNRKT (SEQ ID NO: 49) | TSGSLSR (SEQ ID NO: 50) | QSGHLSR (SEQ ID NO: 41) |
| 19213 PRKCH- cgAAGGTGTCC GAGGCGCCGgtc gtgcg (SEQ ID NO: 51) | RSDTLSE (SEQ ID NO: 52) | RSADLSR (SEQ ID NO: 53) | RSDNLAR (SEQ ID NO: 9) | DSSDRKK (SEQ ID NO: 54) | RSAALSR (SEQ ID NO: 29) | RLDNRTA (SEQ ID NO: 55) |
| 19214 PRKCH- ggGTTGGGTGA GTAGCGgtgaccc cttc (SEQ ID NO: 56) | RSDDLTR (SEQ ID NO: 57) | QSGSLTR (SEQ ID NO: 25) | QNAHRKT (SEQ ID NO: 47) | RSDHLSR (SEQ ID NO: 58) | TSGSLTR (SEQ ID NO: 59 | N/A |
| 12273 CXCR4- ggGTAGAAGCG GTCacagatatatctg t (SEQ ID NO: 60) | DRSALSR (SEQ ID NO: 37) | RSDDLTR (SEQ ID NO: 57) | QSGNLAR (SEQ ID NO: 61) | QSGSLTR (SEQ ID NO: 25) | N/A | N/A |
| 12270 CXCR4- atGACTTGTGGG TGgttgtgttccagtt (SEQ ID NO: 62) | RSDSLLR (SEQ ID NO: 63) | RSDHLTT (SEQ ID NO: 36) | RSDSLSA (SEQ ID NO: 44) | DRSNLTR (SEQ ID NO: 64) | N/A | N/A |

Example 2

Inducing Pre-Defined Deletions: Deletion of 465 bp

To induce a deletion of specified boundaries and length at a predefined target, donors were designed to span the DNA segment to be deleted. In particular, ZFNs were used to create a specific cut at the target site and then a donor with regions of homology on both ends distal to the deletion site is integrated into the specific cut to define the borders and length of the deletion. See, FIG. 1A. One or more different ZFN pairs may be used (e.g., two pairs as shown in FIG. 1A as pair #1 or pair #2).

FIG. 1 shows the details of the target and donor design for the experiment, including the target site within CCR5 (FIG. 1B) and the donor polynucleotide (FIG. 1C), used to create a 465 base pair deletion. K562 cells were transduced with the ZFN encoding pVAX plasmids in various combinations and with the donor on a pCR4 plasmid. Following transformation, genomic DNA was isolated and subject to PCR analysis using primers on the distal sides of the deletion site. The primers used were as follows: R5-HR-F1:

CTGCCTCATAAGGTTGCCCTAAG (SEQ ID NO: 65)

and R5-HR-R1:

CCAGCAATAGATGATCCAACTCAAATTCC. (SEQ ID NO: 66)

Figure 2:
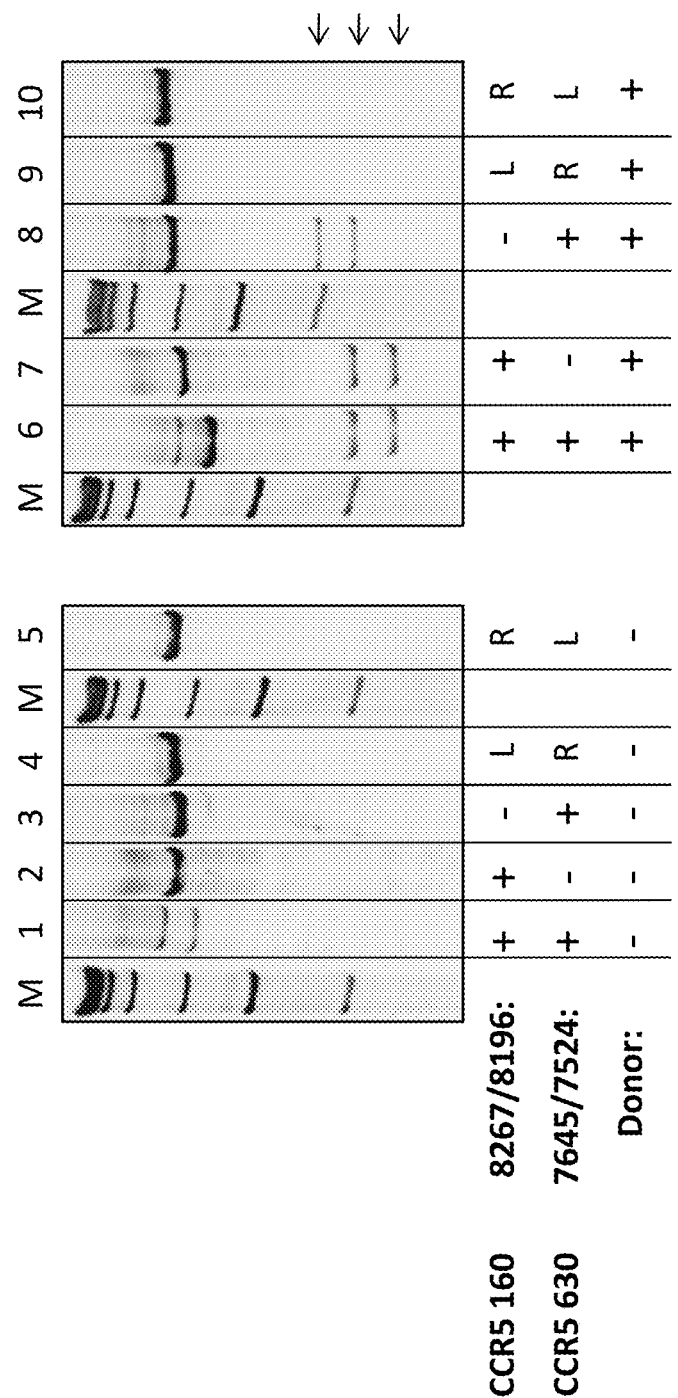
FIG. 2 depicts two gels showing the integration of the donor molecule into two loci (160 and 630) within the CCR5 locus. Experimental constituents (+/−ZFNs and/or donor) are depicted below each lane. The gels show the results following the PCR amplification of the target loci after cleavage with the ZFN pairs, followed by digestion of the PCR product using BamHI. The results demonstrate that the donor has integrated because cleavage with BamHI results in observable cleavage product bands, indicated by the arrows.

The PCR products were analyzed by gel electrophoresis. As shown in FIG. 2, in the presence of the donor, the use of a single ZFN pair and the donor causes the deletion of the desired 465 bp of intervening region along with the insertion of the patch donor carrying the BamHI site. When the donor is present in the reaction, a single ZFN pair at one location causes the insertion of the donor DNA, as evidenced by the cleavage with the BamHI restriction enzyme.

This data demonstrates that although only one side of the deletion is cleaved by the ZFN pair, there is resection of the target that occurs which can be stopped and captured at the desired distance away from the ZFN cleavage site with the donor DNA.

Example 3

Inducing Pre-Defined Deletions: Deletion of 3.8 Kb

To extend this observation to a larger deletion region, two pairs of ZFNs were used in a similar experimental design as that used in Example 2 in K562 cells targeting the POU5F1 locus (POU domain, class 5, transcription factor 1, also known as Oct4). In this example, the donor contained a Sal I restriction site, so if donor insertion has occurred, the resultant locus will be sensitive to Sal I digestion. As described above in Example 1, PCR was used to create a product where the primers were located on either distal side of the region for deletion. The primers used for this experiment were as follows: GJC 208F:

(SEQ ID NO: 67)
5'-AAAGTTTCTGTGGGGGACCT-3' and GJC 211R:

(SEQ ID NO: 68)
5'-CATCCCACTGAGAACCACTG-3'.

The PCR products were amplified and analyzed by gel electrophoresis. As shown in FIG. 3A, the PCR product produced indicate that a deletion occurred when either one or both ZFN pairs were present. As shown in FIG. 3B, Sal I digestion performed on the PCR product showed that the PCR product in all cases was capable of being cleaved by Sal I to some extent. The sample on the left side of the gel showed the results when no donor was used in the first step, and thus all joining of the cut ends was done via NHEJ. In contrast, in the sample where both pair of ZFNs were used and donor was present (far right of the gel), there was PCR product that could not be digested by the Sal I enzyme as well as PCR product that did contain the Sal I site, again illustrating that when both pairs of ZFN are used, NHEJ can occur, but in the presence of donor DNA, insertion via HDR also occurs. In the samples with only one ZFN pair, the predominant product of the PCR is Sal I-cleavable, indicating that HDR occurred in the majority of these samples.

Example 4

Inducing Predefined Deletions: Deletion of >120 Kb

Next, even larger deletions were made through this technique of targeted deletion. For this example, the PRKCH locus (Protein Kinase C, eta type) was chosen. Two sets of ZFNs were produced which target the PRKCH locus where the targets of these ZFNs were approximately 120 Kb apart. As for Examples 2 and 3, PCR primers were chosen on the distal side of the deletion and the donor nucleotide had a Sal I restriction site. The PCR primers are as follows: GJC 223F:

(SEQ ID NO: 69)
5'-CAGCTGCTTCCTGGTTTGAA-3' and GJC 228R:

(SEQ ID NO: 70)
5'-GATCCAAGGGCTTCTGCCTT-3'.

As described above, the ZFNs were transduced into K562 cells and then the genomic DNA isolated and subjected to PCR using the above primers.

The PCR product was then digested with the Sal I restriction enzyme to identify if donor insertion had occurred. As shown in FIG. 4, the targeted deletion is less prevalent than in the previous examples, but bands from the digested donor are present, indicating that the deletion of >120 Kb of DNA followed by the insertion of the donor sequence was possible.

Example 5

Figure 5:
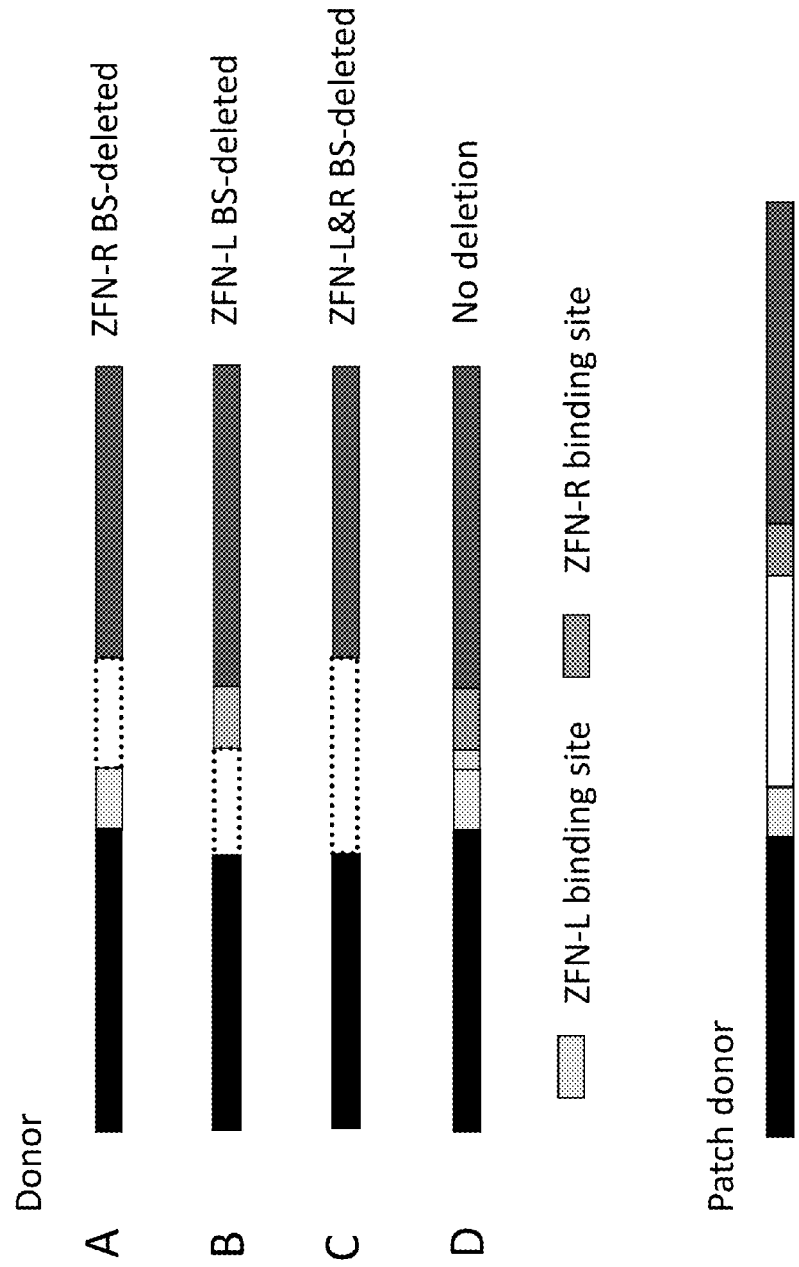
FIG. 5 depicts schematics of the donor types used in Example 5. Donors A-D are the donor types lacking the binding site for either the right-most ZFN (ZFN-R-BS deleted), the left-most ZFN (ZFN-L-BS-deleted) or with both ZFN binding sites deleted (ZFN L&R BS-deleted).

Single Arm Homology Proximal to the ZFN Cleavage Site is Sufficient for Insertion In order to investigate the requirement and location for donor homology for insertion to occur during the targeted deletion, four donor types were constructed containing various combinations of ZFN binding sites and homologous arms. FIG. 5 shows a schematic of the different types of donor constructs. Briefly, Donor A contains the left and right homology arms, and the left ZFN binding site. B contains both homology arms and the right ZFN binding site. C contains only the homology arms, without any of the ZFN binding sites, and Donor D contains both homology arms and both ZFN binding sites, but carries additional sequence in between all elements. In addition, a patch donor was also used containing both ZFN binding sites and a region of 41 bp between.

Figure 6:
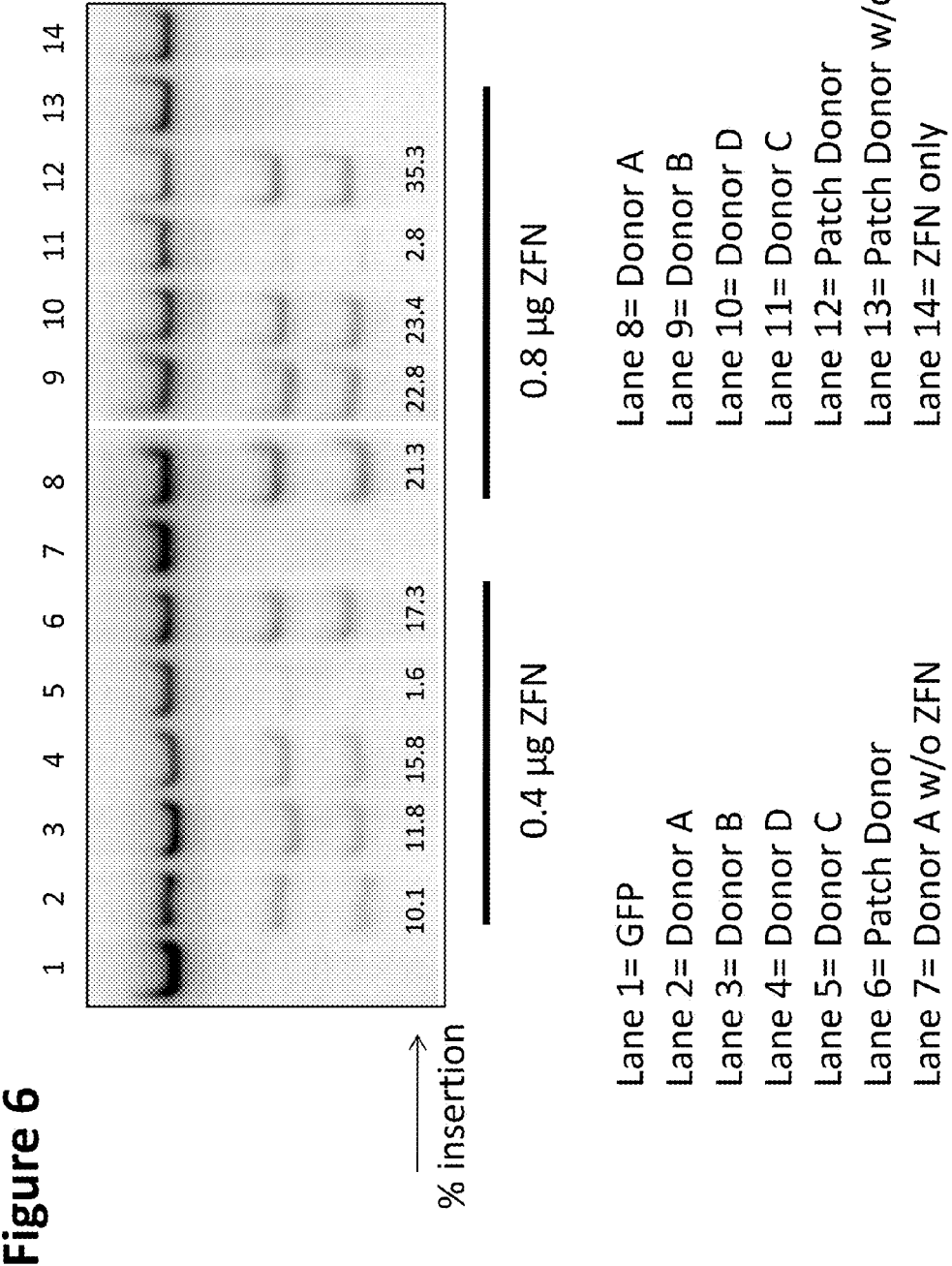
FIG. 6 shows a gel depicting the results of Example 5. The lane identities are shown under the gel. As can be seen from the figure, only one region of ZFN binding homology is necessary and is sufficient for donor integration. Also, increasing the dose of ZFN plasmid increases the percentage of integration observed (indicated at the bottom of the lanes).

The donors were tested using two different doses of ZFN encoding plasmid, 0.4 μg and 0.8 μg and the results are shown in FIG. 6. In all these experiments, the ZFNs chosen were the 12273EL/12270KK pair targeting CXCR4. The primers used for amplifying the product were as follows: X4-out-F1:

(SEQ ID NO: 71)
CCAAGTGATAAACACGAGGATGG and X4-out-R1:

(SEQ ID NO: 72)
CCAGCATTTCTATACCACTTTGG.

The experiment showed that homology directed recombination of the various donors was successful if there was sufficient homology present. For the A, B and D donors, insertion was successful even though the A and B donors only had homology to single ZFN binding sites in the target.

As shown in FIG. 6, there was some insertion of donor C although to a much lower level because the donor homology was farther away from the initial cutting site in the target. Also, a general increase in donor insertion was observed when the amount of ZFN encoding plasmid was increased (compare lanes 2-6 with lanes 8-12 in FIG. 6).

All patents, patent applications and publications mentioned herein are hereby incorporated by reference, in their entireties, for all purposes.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

The invention claimed is:

1. A method for creating a targeted deletion of specific length and specific borders in a region of interest in a genomic locus in a host cell, the method comprising introducing first and second nucleases and a donor polynucleotide into the host cell, wherein
   (i) the first and second nucleases each comprise a 5'DNA-binding domain and a 3' DNA binding domain and two catalytic domains;
   (ii) the first nuclease binds to target sequences 5 to the target sequences in the region of interest bound by the second nuclease;
   (iii) the 5' DNA-binding domain binds to a target sequence 5' to the target sequence bound by the 3' DNA-binding domain,
   (iv); the first nuclease binds to target sequences 5' to the target sequences in the region of interest and the second nuclease binds to target sequences 3' in the region of interest;
   (v) the donor polynucleotide comprises the target sequences for the 5' DNA binding domain of the first nuclease and target sequences for the 3' DNA binding domain of the second nuclease and regions of homology to the genomic locus and further wherein the donor polynucleotide includes a deletion relative to the target sequence of specific length and specific borders, wherein the deletion extends between the target sequence 5' DNA binding domain in of the first nuclease and target sequence for the 3' DNA binding domain of the second nuclease; and
   (vi) the donor polynucleotide is introduced into the genomic locus such that a targeted deletion of specific length and specific borders is generated in the genomic locus.

2. The method of claim 1, wherein the regions of homology are between about 50 and 1500 base pairs in length.

3. The method of claim 1, wherein the first nuclease cleaves at a first location and the second nuclease cleaves at a second location.

4. The method of claim 1, wherein between the regions of homology, the donor polynucleotide comprises a sequence selected from the group consisting of a coding sequence, a 2A peptide, an SA site, an internal ribosome entry site (IRES), a shRNA molecule, an miRNA molecule, an RNAi and combinations thereof.

5. The method of claim 1, wherein the host cell is a eukaryotic cell.

6. The method of claim 5, wherein the eukaryotic cell is a mammalian or plant cell.

* * * * *